United States Patent
Taniguchi et al.

(10) Patent No.: US 11,966,161 B2
(45) Date of Patent: Apr. 23, 2024

(54) RADIATION-SENSITIVE RESIN COMPOSITION, METHOD OF FORMING RESIST PATTERN, AND COMPOUND

(71) Applicant: JSR CORPORATION, Tokyo (JP)

(72) Inventors: Takuhiro Taniguchi, Tokyo (JP); Katsuaki Nishikori, Tokyo (JP); Hayato Namai, Tokyo (JP); Kazuya Kiriyama, Tokyo (JP); Ken Maruyama, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 17/854,048

(22) Filed: Jun. 30, 2022

(65) Prior Publication Data

US 2022/0334481 A1 Oct. 20, 2022
US 2023/0244143 A9 Aug. 3, 2023

Related U.S. Application Data

(63) Continuation of application No. PCT/JP2020/043447, filed on Nov. 20, 2020.

(30) Foreign Application Priority Data

Jan. 7, 2020 (JP) .................................. 2020-000877

(51) Int. Cl.
  *G03F 7/004* (2006.01)
  *C07C 303/32* (2006.01)
  *C07C 381/12* (2006.01)
  *C08G 75/20* (2016.01)
  *G03F 7/039* (2006.01)

(52) U.S. Cl.
  CPC .......... *G03F 7/0045* (2013.01); *C07C 303/32* (2013.01); *C07C 381/12* (2013.01); *C08G 75/20* (2013.01); *G03F 7/0392* (2013.01); *G03F 7/0397* (2013.01)

(58) Field of Classification Search
  CPC .... G03F 7/0045; G03F 7/0392; G03F 7/0397; C07C 381/12; C07C 303/32
  See application file for complete search history.

(56) References Cited

U.S. PATENT DOCUMENTS

| | | | | |
|---|---|---|---|---|
| 7,217,492 B2* | 5/2007 | Yoneda | ................. | G03F 7/0757 |
| | | | | 564/92 |
| 2006/0194147 A1* | 8/2006 | Kawanishi | ............ | G03F 7/0045 |
| | | | | 430/270.1 |
| 2011/0152540 A1* | 6/2011 | Nakayashiki | .......... | C09K 15/10 |
| | | | | 562/113 |
| 2012/0164582 A1* | 6/2012 | Maruyama | .............. | C08F 20/28 |
| | | | | 562/113 |

(Continued)

FOREIGN PATENT DOCUMENTS

| | | |
|---|---|---|
| JP | S59-93448 A | 5/1984 |
| JP | H06-12452 B2 | 2/1994 |
| JP | 2009134088 A | 6/2009 |

(Continued)

OTHER PUBLICATIONS

International Search Report dated Jan. 26, 2021 in PCT/JP2020/043447 (with English translation), 5 pages.

(Continued)

*Primary Examiner* — John S Chu
(74) *Attorney, Agent, or Firm* — Element IP, PLC

(57) ABSTRACT

A radiation-sensitive resin composition includes: a polymer including a structural unit including an acid-labile group; and a compound represented by formula (1). $R^1$, $R^2$, and $R^3$ each independently represent a halogen atom, a hydroxy group, a nitro group, or a monovalent organic group having 1 to 20 carbon atoms; $X^1$, $X^2$, and $X^3$ each independently represent a group represented by formula (2); a sum of d, e, and f is no less than 1; $R^4$ represents a hydrocarbon group having 1 to 20 carbon atoms and $R^5$ represents a hydrocarbon group having 1 to 20 carbon atoms, or $R^4$ and $R^5$ taken together represent a heterocyclic structure having 4 to 20 ring atoms, together with the sulfur atom to which $R^4$ and $R^5$ bond; n is 0 or 1; $A^-$ represents a monovalent sulfonic acid anion; and Y represents —COO—, —OCO—, or —N($R^7$)CO—.

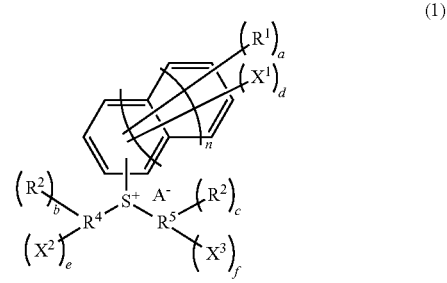

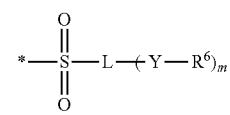

19 Claims, No Drawings

(56) References Cited

U.S. PATENT DOCUMENTS

2013/0230804 A1* 9/2013 Sakakibara ........... C07C 381/12
  430/281.1
2021/0188770 A1* 6/2021 Fujiwara ................ C07C 69/63

FOREIGN PATENT DOCUMENTS

| | | |
|---|---|---|
| JP | 2010134279 A | 6/2010 |
| JP | 2014224984 A | 12/2014 |
| JP | 2016047815 A | 4/2016 |
| TW | 201910311 A | 3/2019 |

OTHER PUBLICATIONS

Written Opinion dated Jan. 26, 2021 in PCT/JP2020/043447 (with English translation), 6 pages.
Combined Taiwanese Office Action and Search Report dated Nov. 28, 2023, received Dec. 21, 2023, in corresponding Taiwanese Patent Application No. 109140161 (with English translation), 18 pages.

* cited by examiner

RADIATION-SENSITIVE RESIN COMPOSITION, METHOD OF FORMING RESIST PATTERN, AND COMPOUND

CROSS-REFERENCE TO RELATED APPLICATIONS

The present application is a continuation application of International Application No. PCT/JP2020/043447, filed Nov. 20, 2020, which claims priority to Japanese Patent Application No. 2020-000877, filed Jan. 7, 2020. The contents of these applications are incorporated herein by reference in their entirety.

FIELD OF THE INVENTION

The present invention relates to a radiation-sensitive resin composition, a method of forming a resist pattern, and a compound.

DESCRIPTION OF THE RELATED ART

A radiation-sensitive resin composition for use in microfabrication by lithography generates an acid at light-exposed regions upon an irradiation with a radioactive ray, e.g., an electromagnetic wave such as a far ultraviolet ray such as an ArF excimer laser beam (wavelength of 193 nm), a KrF excimer laser beam (wavelength of 248 nm), etc. or an extreme ultraviolet ray (EUV) (wavelength of 13.5 nm), or a charged particle ray such as an electron beam. A chemical reaction in which the acid serves as a catalyst causes a difference between the light-exposed regions and light-unexposed regions in rates of dissolution in a developer solution, whereby a resist pattern is formed on a substrate.

Such radiation-sensitive compositions are required not only to have favorable sensitivity to exposure light such as an extreme ultraviolet ray and an electron beam, but also to result in superiority in terms of CDU (Critical Dimension Uniformity) performance and LWR (Line Width Roughness) performance.

Types, molecular structures, and the like of polymers, acid generating agents, and other components which may be used in radiation-sensitive resin compositions have been investigated to meet these requirements, and combinations thereof have been further investigated in detail (see Japanese Unexamined Patent Applications, Publication Nos. 2010-134279, 2014-224984, and 2016-047815).

SUMMARY OF THE INVENTION

According to an aspect of the present invention, a radiation-sensitive resin composition includes: a polymer including a structural unit including an acid-labile group; and a compound represented by formula (1).

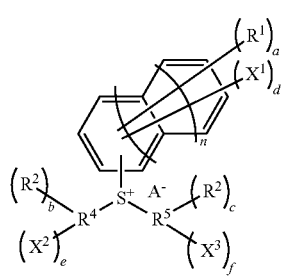
(1)

In the formula (1), $R^1$, $R^2$, and $R^3$ each independently represent a halogen atom, a hydroxy group, a nitro group, or a monovalent organic group having 1 to 20 carbon atoms; a is an integer of 0 to 7, wherein in a case in which a is no less than 2, a plurality of $R^1$s are identical or different from each other; b is an integer of 0 to 4, wherein in a case in which b is no less than 2, a plurality of $R^2$s are identical or different from each other; c is an integer of 0 to 4, wherein in a case in which c is no less than 2, a plurality of $R^1$s are identical or different from each other; $X^1$, $X^2$, and $X^3$ each independently represent a group represented by formula (2); d is an integer of 0 to 7, wherein in a case in which d is no less than 2, a plurality of $X^1$s are identical or different from each other; e is an integer of 0 to 4, wherein in a case in which e is no less than 2, a plurality of $X^2$s are identical or different from each other; f is an integer of 0 to 4, wherein in a case in which f is no less than 2, a plurality of $X^3$s are identical or different from each other, wherein a sum of d, e, and f is no less than 1, a sum of a and d is no greater than 7, a sum of b and e is no greater than 4, and a sum of c and f is no greater than 4; $R^4$ represents a hydrocarbon group having 1 to 20 carbon atoms and having a valency of (b+e+1) and $R^5$ represents a hydrocarbon group having 1 to 20 carbon atoms and having a valency of (c+f+1), or $R^4$ and $R^5$ taken together represent a heterocyclic structure having 4 to 20 ring atoms, together with the sulfur atom to which $R^4$ and $R^5$ bond; n is 0 or 1; and $A^-$ represents a monovalent sulfonic acid anion.

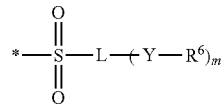
(2)

In the formula (2), L represents an organic group having 1 to 20 carbon atoms and having a valency of (m+1); Y represents —COO—, —OCO—, or —N($R^7$)CO—, wherein $R^7$ represents a hydrogen atom or a monovalent hydrocarbon group having 1 to 20 carbon atoms; $R^6$ represents a monovalent organic group having 1 to 20 carbon atoms; m is an integer of 1 to 5, wherein in a case in which m is no less than 2, a plurality of Ys are identical or different and a plurality of $R^6$s are identical or different; and * denotes a site of bonding to a part other than the group represented by the formula (2) in the compound.

According to another aspect of the present invention, a method of forming a resist pattern includes: applying a radiation-sensitive resin composition directly or indirectly on a substrate to form a resist film; exposing the resist film; and developing the resist film exposed. The radiation-sensitive resin composition includes: a polymer including a structural unit including an acid-labile group; and a compound represented by formula (1).

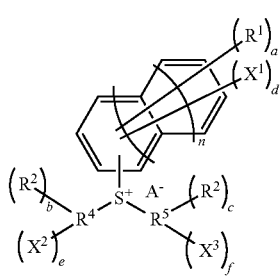
(1)

In the formula (1), $R^1$, $R^2$, and $R^3$ each independently represent a halogen atom, a hydroxy group, a nitro group, or a monovalent organic group having 1 to 20 carbon atoms; a is an integer of 0 to 7, wherein in a case in which a is no less than 2, a plurality of $R^1$s are identical or different from each other; b is an integer of 0 to 4, wherein in a case in which b is no less than 2, a plurality of $R^2$s are identical or different from each other; c is an integer of 0 to 4, wherein in a case in which c is no less than 2, a plurality of $R^1$s are identical or different from each other; $X^1$, $X^2$, and $X^3$ each independently represent a group represented by formula (2); d is an integer of 0 to 7, wherein in a case in which d is no less than 2, a plurality of $X^1$s are identical or different from each other; e is an integer of 0 to 4, wherein in a case in which e is no less than 2, a plurality of $X^2$s are identical or different from each other; f is an integer of 0 to 4, wherein in a case in which f is no less than 2, a plurality of $X^3$s are identical or different from each other, wherein a sum of d, e, and f is no less than 1, a sum of a and d is no greater than 7, a sum of b and e is no greater than 4, and a sum of c and f is no greater than 4; $R^4$ represents a hydrocarbon group having 1 to 20 carbon atoms and having a valency of (b+e+1) and $R^5$ represents a hydrocarbon group having 1 to 20 carbon atoms and having a valency of (c+f+1), or $R^4$ and $R^5$ taken together represent a heterocyclic structure having 4 to 20 ring atoms, together with the sulfur atom to which $R^4$ and $R^5$ bond; n is 0 or 1; and $A^-$ represents a monovalent sulfonic acid anion.

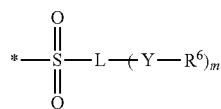

(2)

In the formula (2), L represents an organic group having 1 to 20 carbon atoms and having a valency of (m+1); Y represents —COO—, —OCO—, or —N($R^7$)CO—, wherein $R^7$ represents a hydrogen atom or a monovalent hydrocarbon group having 1 to 20 carbon atoms; $R^6$ represents a monovalent organic group having 1 to 20 carbon atoms; m is an integer of 1 to 5, wherein in a case in which m is no less than 2, a plurality of Ys are identical or different and a plurality of $R^6$s are identical or different; and * denotes a site of bonding to a part other than the group represented by the formula (2) in the compound.

According to a further aspect of the present invention, a compound is represented by formula (1).

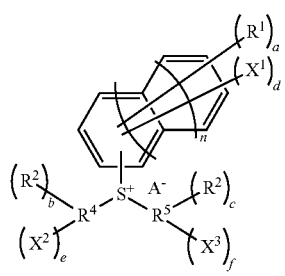

(1)

In the formula (1), $R^1$, $R^2$, and $R^3$ each independently represent a halogen atom, a hydroxy group, a nitro group, or a monovalent organic group having 1 to 20 carbon atoms; a is an integer of 0 to 7, wherein in a case in which a is no less than 2, a plurality of $R^1$s are identical or different from each other; b is an integer of 0 to 4, wherein in a case in which b is no less than 2, a plurality of $R^2$s are identical or different from each other; c is an integer of 0 to 4, wherein in a case in which c is no less than 2, a plurality of $R^3$s are identical or different from each other; $X^1$, $X^2$, and $X^3$ each independently represent a group represented by formula (2); d is an integer of 0 to 7, wherein in a case in which d is no less than 2, a plurality of $X^1$s are identical or different from each other; e is an integer of 0 to 4, wherein in a case in which e is no less than 2, a plurality of $X^2$s are identical or different from each other; f is an integer of 0 to 4, wherein in a case in which f is no less than 2, a plurality of $X^3$s are identical or different from each other, wherein a sum of d, e, and f is no less than 1, a sum of a and d is no greater than 7, a sum of b and e is no greater than 4, and a sum of c and f is no greater than 4; $R^4$ represents a hydrocarbon group having 1 to 20 carbon atoms and having a valency of (b+e+1) and $R^5$ represents a hydrocarbon group having 1 to 20 carbon atoms and having a valency of (c+f+1), or $R^4$ and $R^5$ taken together represent a heterocyclic structure having 4 to 20 ring atoms, together with the sulfur atom to which $R^4$ and $R^5$ bond; n is 0 or 1; and $A^-$ represents a monovalent sulfonic acid anion.

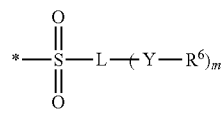

(2)

In the formula (2), L represents an organic group having 1 to 20 carbon atoms and having a valency of (m+1); Y represents —COO—, —OCO—, or —N($R^7$)CO—, wherein $R^7$ represents a hydrogen atom or a monovalent hydrocarbon group having 1 to 20 carbon atoms; $R^6$ represents a monovalent organic group having 1 to 20 carbon atoms; m is an integer of 1 to 5, wherein in a case in which m is no less than 2, a plurality of Ys are identical or different and a plurality of $R^6$s are identical or different; and * denotes a site of bonding to a part other than the group represented by the formula (2) in the compound.

DESCRIPTION OF THE EMBODIMENTS

As used herein, the words "a" and "an" and the like carry the meaning of "one or more." When an amount, concentration, or other value or parameter is given as a range, and/or its description includes a list of upper and lower values, this is to be understood as specifically disclosing all integers and fractions within the given range, and all ranges formed from any pair of any upper and lower values, regardless of whether subranges are separately disclosed. Where a range of numerical values is recited herein, unless otherwise stated, the range is intended to include the endpoints thereof, as well as all integers and fractions within the range. As an example, a stated range of 1-10 fully describes and includes the independent subrange 3.4-7.2 as does the following list of values: 1, 4, 6, 10.

Under current circumstances in which miniaturization of resist patterns has proceeded to a level in which line widths are 40 nm or less, required levels for the aforementioned types of performance are further elevated.

According to one embodiment of the invention made for solving the aforementioned problems, a radiation-sensitive resin composition contains: a polymer (hereinafter, may be also referred to as "(A) polymer" or "polymer (A)") having a structural unit including an acid-labile group; and a compound (hereinafter, may be also referred to as "(B) compound" or "compound (B)") represented by the following formula (1):

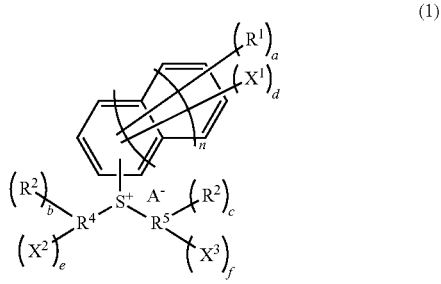

wherein, in the formula (1),
$R^1$, $R^2$, and $R^3$ each independently represent a halogen atom, a hydroxy group, a nitro group, or a monovalent organic group having 1 to 20 carbon atoms;
a is an integer of 0 to 7, wherein in a case in which a is no less than 2, a plurality of $R^1$s are identical or different from each other;
b is an integer of 0 to 4, wherein in a case in which b is no less than 2, a plurality of $R^2$s are identical or different from each other;
c is an integer of 0 to 4, wherein in a case in which c is no less than 2, a plurality of $R^1$s are identical or different from each other;
$X^1$, $X^2$, and $X^3$ each independently represent a group represented by formula (2);
d is an integer of 0 to 7, wherein in a case in which d is no less than 2, a plurality of $X^1$s are identical or different from each other;
e is an integer of 0 to 4, wherein in a case in which e is no less than 2, a plurality of $X^2$s are identical or different from each other;
f is an integer of 0 to 4, wherein in a case in which f is no less than 2, a plurality of $X^3$s are identical or different from each other,
wherein a sum of d, e, and f is no less than 1, a sum of a and d is no greater than 7, a sum of b and e is no greater than 4, and a sum of c and f is no greater than 4;
$R^4$ represents a hydrocarbon group having 1 to 20 carbon atoms and having a valency of (b+e+1) and $R^5$ represents a hydrocarbon group having 1 to 20 carbon atoms and having a valency of (c+f+1), or $R^4$ and $R^5$ taken together represent a heterocyclic structure having 4 to 20 ring atoms, together with the sulfur atom to which $R^4$ and $R^5$ bond;
n is 0 or 1; and
$A^-$ represents a monovalent sulfonic acid anion,

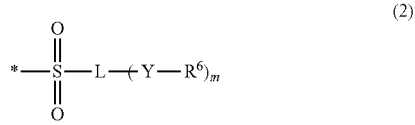

wherein, in the above formula (2),
L represents an organic group having 1 to 20 carbon atoms and having a valency of (m+1);
Y represents —COO—, —OCO—, or —N($R^7$)CO—, wherein $R^7$ represents a hydrogen atom or a monovalent hydrocarbon group having 1 to 20 carbon atoms;
$R^6$ represents a monovalent organic group having 1 to 20 carbon atoms;
m is an integer of 1 to 5, wherein in a case in which m is no less than 2, a plurality of Ys are identical or different and a plurality of $R^1$s are identical or different; and
* denotes a site of bonding to a part other than the group represented by the formula (2) in the compound.

According to an other embodiment of the invention made for solving the aforementioned problems, a method of forming a resist pattern includes: applying the radiation-sensitive resin composition of the one embodiment of the present invention directly or indirectly on a substrate; exposing a resist film formed by the applying; and developing the resist film exposed.

Still another embodiment of the invention made for solving the aforementioned problems is a compound represented by the above formula (1).

The radiation-sensitive resin composition and the method of forming a resist pattern of the embodiments of the present invention enable a resist pattern to be formed with favorable sensitivity to exposure light and superiority in terms of CDU performance and LWR performance. The compound of the still another embodiment of the present invention can be suitably used as a component of the radiation-sensitive resin composition of the one embodiment of the present invention. Therefore, the radiation-sensitive resin composition, the method of forming a resist pattern, and the compound can be suitably used for working processes of semiconductor devices, and the like, in which microfabrication is expected to be further in progress hereafter.

Hereinafter, the radiation-sensitive resin composition, the method of forming a resist pattern, and the compound of embodiments of the present invention will be described in detail.

Radiation-Sensitive Resin Composition

The radiation-sensitive composition of the one embodiment of the present invention contains the polymer (A) and the compound (B). The radiation-sensitive resin composition typically contains an organic solvent (hereinafter, may be also referred to as "(D) organic solvent" or "organic solvent (D)"). The radiation-sensitive composition may contain, as a favorable component, an acid diffusion control agent (hereinafter, may be also referred to as "(C) acid diffusion control agent" or "acid diffusion control agent (C)") and/or a polymer (hereinafter, may be also referred to as "(E) polymer" or "polymer (E)") having a mass percentage content of fluorine atoms greater than that of the polymer (A). The radiation-sensitive resin composition may contain, within a range not leading to impairment of the effects of the present invention, other optional component(s).

Due to the polymer (A) and the compound (B) being contained, the radiation-sensitive resin composition enables a resist pattern to be formed with favorable sensitivity to exposure light and superiority in terms of the CDU performance and the LWR performance. Although not necessarily clarified and without wishing to be bound by any theory, the reason for achieving the aforementioned effects by the radiation-sensitive resin composition due to involving such a constitution may be presumed, for example, as in the following. It is believed that due to a cation including the group represented by the above formula (2), in the compound (B) contained in the radiation-sensitive resin composition, introduction of substituents having a variety of functions is enabled without a loss of efficiency of generating the acid upon exposure. It is considered that as a result, the radiation-sensitive resin composition of the one embodiment of the present invention enables a resist pattern to be formed with favorable sensitivity to exposure light and superiority in terms of the CDU performance and the LWR performance.

Each component contained in the radiation-sensitive resin composition is described below.

(A) Polymer

The polymer (A) has a structural unit (hereinafter, may be also referred to as "structural unit (I)") including an acid-labile group. The polymer (A) preferably further has a structural unit (hereinafter, may be also referred to as "structural unit (II)") including a lactone structure, a cyclic carbonate structure, a sultone structure, or a combination thereof. The polymer (A) preferably further has a structural unit (hereinafter, may be also referred to as "structural unit (III)") including a phenolic hydroxyl group. The polymer (A) may further have other structural unit(s) (hereinafter, may be also referred to as merely "other structural unit") aside from the structural units (I) to (III). The polymer (A) may have one, or two or more types of each structural unit. The radiation-sensitive resin composition may contain one, or two or more types of the polymer (A).

Each structural unit contained in the polymer (A) is described below.

Structural Unit (I)

The structural unit (1) is a structural unit including an acid-labile group. The "acid-labile group" as referred to herein means a group that substitutes for a hydrogen atom in a carboxy group, a hydroxy group, or the like, and is capable of being dissociated by an action of an acid to give a carboxy group, a hydroxy group, or the like. The acid-labile group is dissociated by an action of the acid generated from the compound (B), etc. upon exposure, whereby the solubility of the polymer (A) in the developer solution is altered in light-exposed regions, and thus a resist pattern can be formed.

Examples of the structural unit (I) include a structural unit (hereinafter, may be also referred to as "structural unit (I-1)") represented by the following formula (3), and the like. It is to be noted that in the following formula (3), —C($R^X$)($R^Y$)($R^Z$), which bonds to an oxy-oxygen atom derived from the carboxy group, corresponds to the acid-labile group.

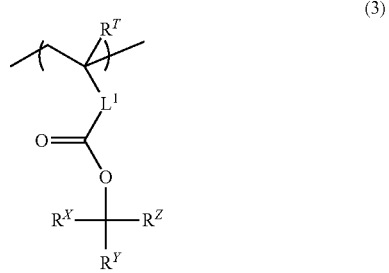

(3)

In the above formula (3),
$R^T$ represents a hydrogen atom, a fluorine atom, a methyl group, or a trifluoromethyl group;
$R^X$ represents a hydrogen atom or a monovalent hydrocarbon group having 1 to 20 carbon atoms;

$R^Y$ and $R^Z$ each independently represent a monovalent hydrocarbon group having 1 to 20 carbon atoms, or $R^Y$ and $R^Z$ taken together represent an alicyclic structure having 3 to 20 ring atoms, together with the carbon atom to which $R^Y$ and $R^Z$ bond; and $L^1$ represents a single bond or a divalent organic group having 1 to 20 carbon atoms.

As referred to herein, the number of "carbon atoms" means the number of carbon atoms constituting a group.

The "hydrocarbon group" as referred to herein may be exemplified by a chain hydrocarbon group, an alicyclic hydrocarbon group, and an aromatic hydrocarbon group. The "hydrocarbon group" may be either a saturated hydrocarbon group or an unsaturated hydrocarbon group. The "chain hydrocarbon group" as referred to herein means a hydrocarbon group not including a ring structure but being constituted with only a chain structure, and may be exemplified by both a linear hydrocarbon group and a branched hydrocarbon group. The "alicyclic hydrocarbon group" as referred to herein means a hydrocarbon group including, as a ring structure, not an aromatic ring structure but an alicyclic structure alone, and may be exemplified by both a monocyclic alicyclic hydrocarbon group and a polycyclic alicyclic hydrocarbon group. With regard to this, it is not necessary for the alicyclic hydrocarbon group to be constituted with only an alicyclic structure; it may include a chain structure in a part thereof. The "aromatic hydrocarbon group" as referred to herein means a hydrocarbon group including an aromatic ring structure as a ring structure. With regard to this, it is not necessary for the aromatic hydrocarbon group to be constituted with only an aromatic ring structure; it may include a chain structure or an alicyclic structure in a part thereof.

As referred to herein, the "organic group" means a group that includes at least one carbon atom.

The monovalent hydrocarbon group having 1 to 20 carbon atoms which may be represented by $R^X$, $R^Y$, or $R^Z$ may be exemplified by a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 20 carbon atoms include: alkyl groups such as a methyl group, an ethyl group, an n-propyl group, and an i-propyl group; alkenyl groups such as an ethenyl group, a propenyl group, and a butenyl group; alkynyl groups such as an ethynyl group, a propynyl group, and a butynyl group; and the like.

Examples of the monovalent alicyclic hydrocarbon group having 3 to 20 carbon atoms include: monocyclic alicyclic saturated hydrocarbon groups such as a cyclopentyl group and a cyclohexyl group; polycyclic alicyclic saturated hydrocarbon groups such as a norbornyl group, an adamantyl group, a tricyclodecyl group, and a tetracyclododecyl group; monocyclic alicyclic unsaturated hydrocarbon groups such as a cyclopentenyl group and a cyclohexenyl group; polycyclic alicyclic unsaturated hydrocarbon groups such as a norbornenyl group, a tricyclodecenyl group, and a tetracyclododecenyl group; and the like.

Examples of the monovalent aromatic hydrocarbon group having 6 to 20 carbon atoms include: aryl groups such as a phenyl group, a tolyl group, a xylyl group, a naphthyl group, and an anthryl group; aralkyl groups such as a benzyl group, a phenethyl group, a naphthylmethyl group, and an anthrylmethyl group; and the like.

Examples of the alicyclic structure having 3 to 20 ring atoms which may be represented by $R^Y$ and $R^Z$ taken together, together with the carbon atom to which $R^Y$ and $R^Z$ bond, include: monocyclic saturated alicyclic structures such as a cyclopropane structure, a cyclobutane structure, a cyclopentane structure, a cyclohexane structure, a cycloheptane structure, and a cyclooctane structure; polycyclic saturated alicyclic structures such as a norbornane structure, an adamantane structure, a tricyclodecane structure, and a tetracyclododecane structure; monocyclic unsaturated alicyclic structures such as a cyclopropene structure, a cyclobutene structure, a cyclopentene structure, and a cyclohexene structure; polycyclic unsaturated alicyclic structures such as a norbornene structure, a tricyclodecene structure, and a tetracyclododecene structure; and the like.

The divalent organic group having 1 to 20 carbon atoms which may be represented by $L^1$ is exemplified by: a divalent hydrocarbon group having 1 to 20 carbon atoms; a group (α) including a divalent heteroatom-containing group between two adjacent carbon atoms of the monovalent hydrocarbon group; a group (β) obtained by substituting with a monovalent heteroatom-containing group, a part or all of hydrogen atoms included in the monovalent hydrocarbon group or the group (α); a group (γ) in which the monovalent hydrocarbon group, the group (α), or the group (β) is combined with a divalent heteroatom-containing group; and the like.

The divalent hydrocarbon group having 1 to 20 carbon atoms is exemplified by groups obtained by removing one hydrogen atom from each of the groups exemplified as the monovalent hydrocarbon group having 1 to 20 carbon atoms which may be represented by $R^X$, $R^Y$, or $R^Z$.

The heteroatom that may constitute the monovalent or divalent heteroatom-containing group is exemplified by an oxygen atom, a nitrogen atom, a sulfur atom, a phosphorus atom, a silicon atom, a halogen atom, and the like. Examples of the halogen atom include a fluorine atom, a chlorine atom, a bromine atom, and an iodine atom.

Examples of the divalent heteroatom-containing group include —O—, —CO—, —S—, —CS—, —NR'—, groups in which at least two of the aforementioned groups are combined, and the like, wherein R' represents a hydrogen atom or a monovalent hydrocarbon group.

In light of copolymerizability of a monomer that gives the structural unit (I), $R^T$ represents preferably a hydrogen atom or a methyl group.

- $R^X$ represents preferably the chain hydrocarbon group or the aromatic hydrocarbon group, and more preferably the alkyl group or the aryl group.
- $R^Y$ and $R^Z$ each preferably represent the chain hydrocarbon group or the alicyclic hydrocarbon group, or $R^Y$ and $R^Z$ taken together preferably represent a saturated alicyclic structure, together with the carbon atom to which $R^Y$ and $R^Z$ bond.
- $L^1$ represents preferably a single bond or a group in which the divalent hydrocarbon group is combined with the divalent heteroatom-containing group.

The structural unit (I-1) is preferably a structural unit (hereinafter, may be also referred to as structural units (I-1-1) to (I-1-8)) represented by the following formulae (3-1) to (3-8).

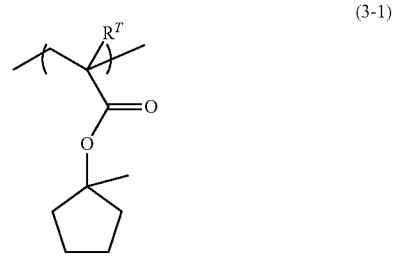

(3-1)

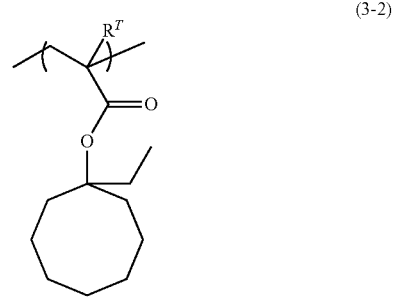

(3-2)

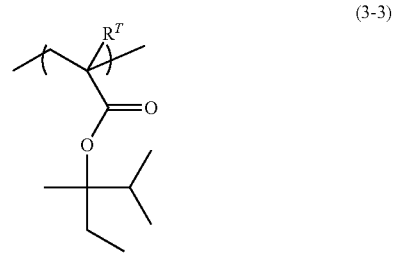

(3-3)

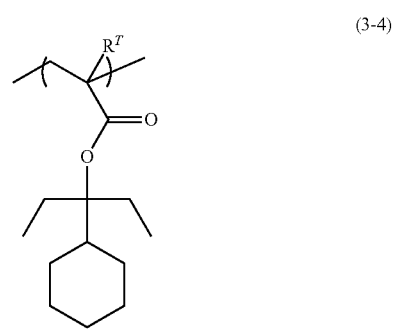

(3-4)

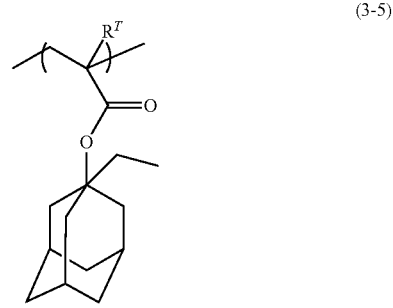

(3-5)

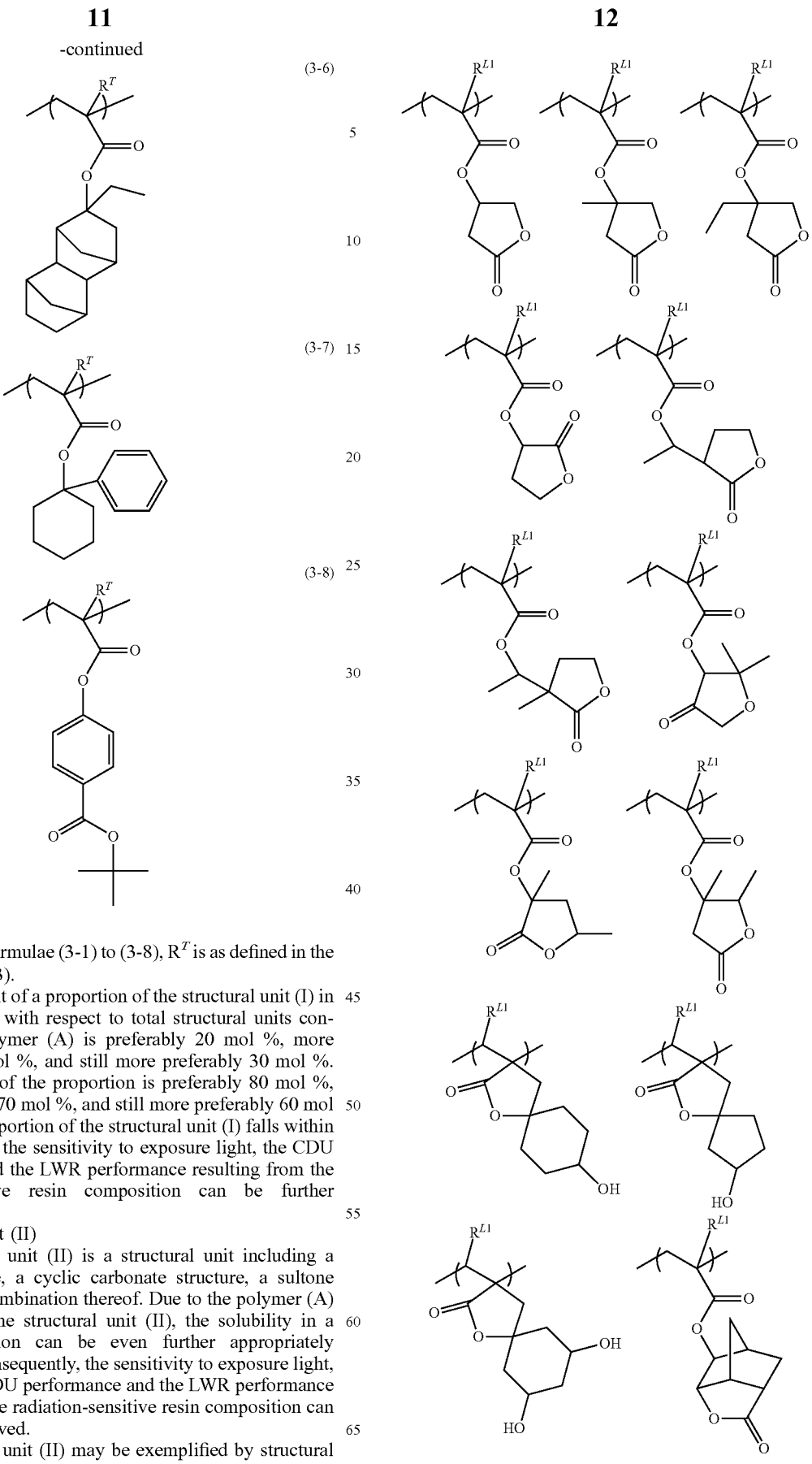

In the above formulae (3-1) to (3-8), $R^T$ is as defined in the above formula (3).

The lower limit of a proportion of the structural unit (I) in the polymer (A) with respect to total structural units constituting the polymer (A) is preferably 20 mol %, more preferably 25 mol %, and still more preferably 30 mol %. The upper limit of the proportion is preferably 80 mol %, more preferably 70 mol %, and still more preferably 60 mol %. When the proportion of the structural unit (I) falls within the above range, the sensitivity to exposure light, the CDU performance, and the LWR performance resulting from the radiation-sensitive resin composition can be further improved.

Structural Unit (II)

The structural unit (II) is a structural unit including a lactone structure, a cyclic carbonate structure, a sultone structure, or a combination thereof. Due to the polymer (A) further having the structural unit (II), the solubility in a developer solution can be even further appropriately adjusted, and consequently, the sensitivity to exposure light, as well as the CDU performance and the LWR performance resulting from the radiation-sensitive resin composition can be further improved.

The structural unit (II) may be exemplified by structural units represented by the following formulae, and the like.

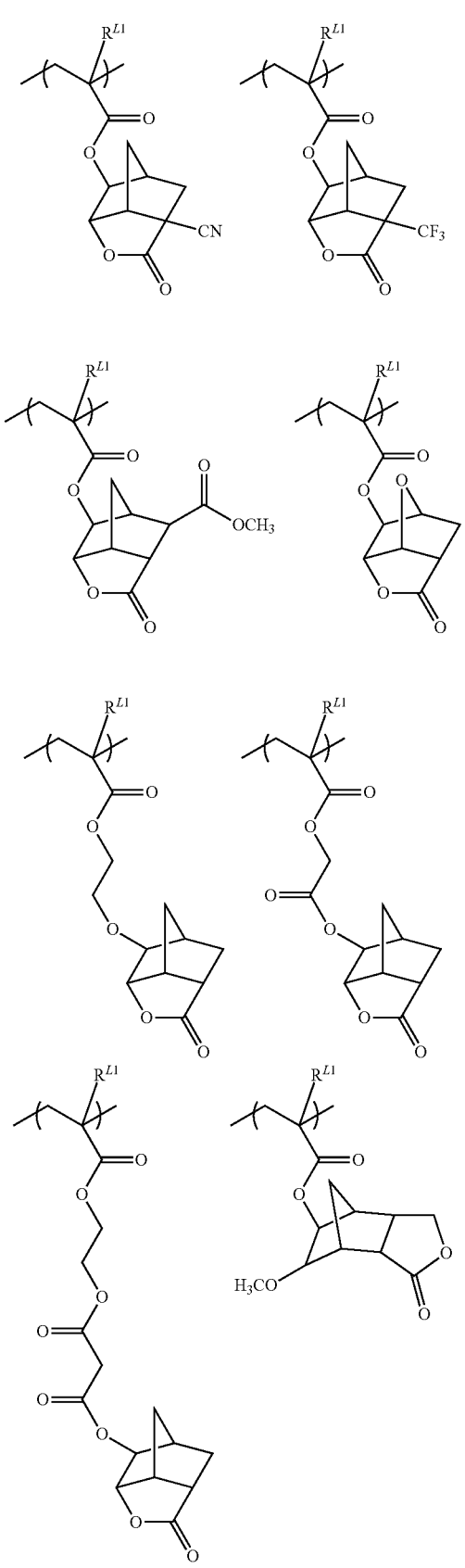
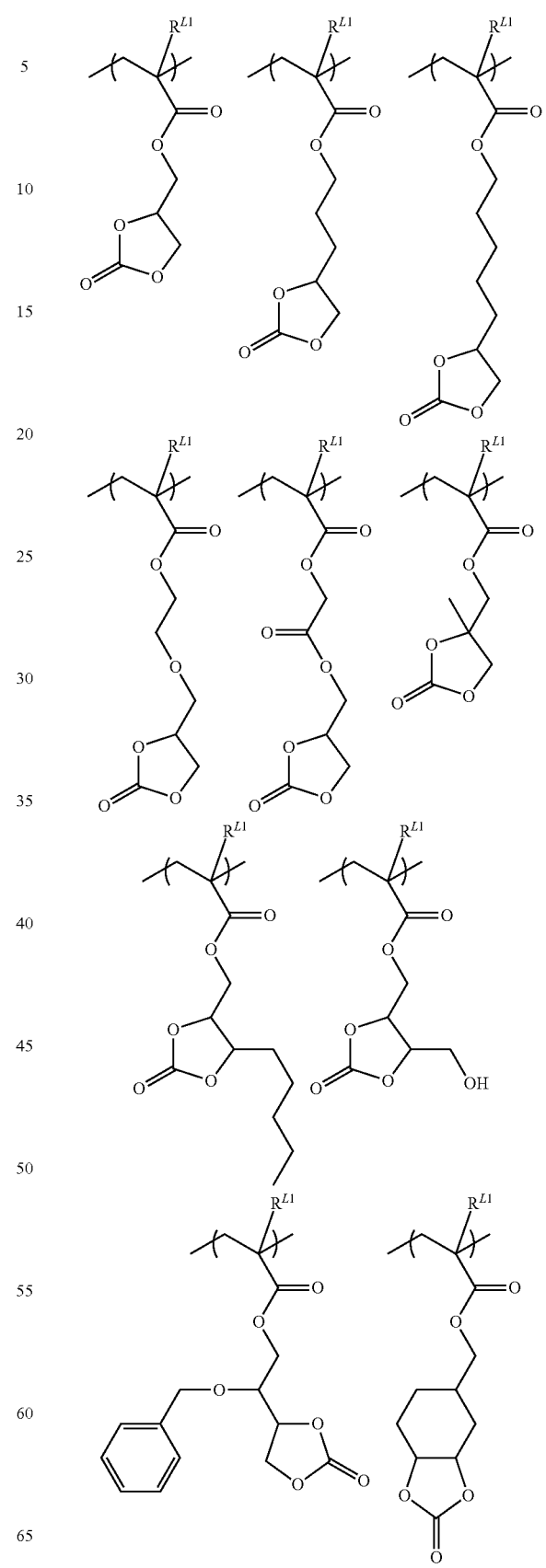

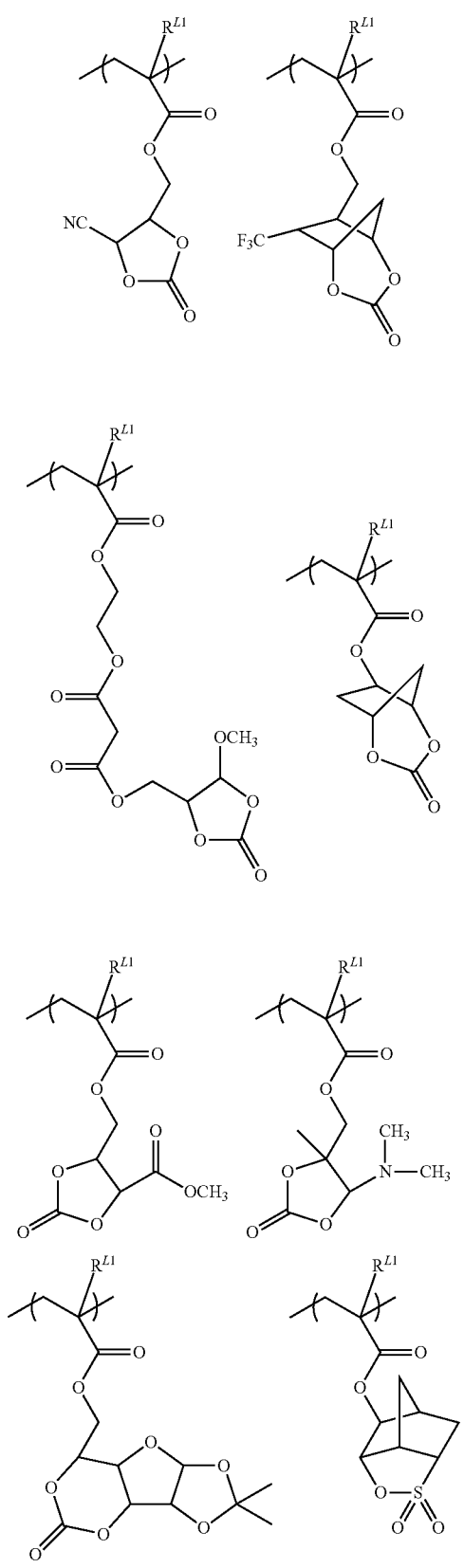
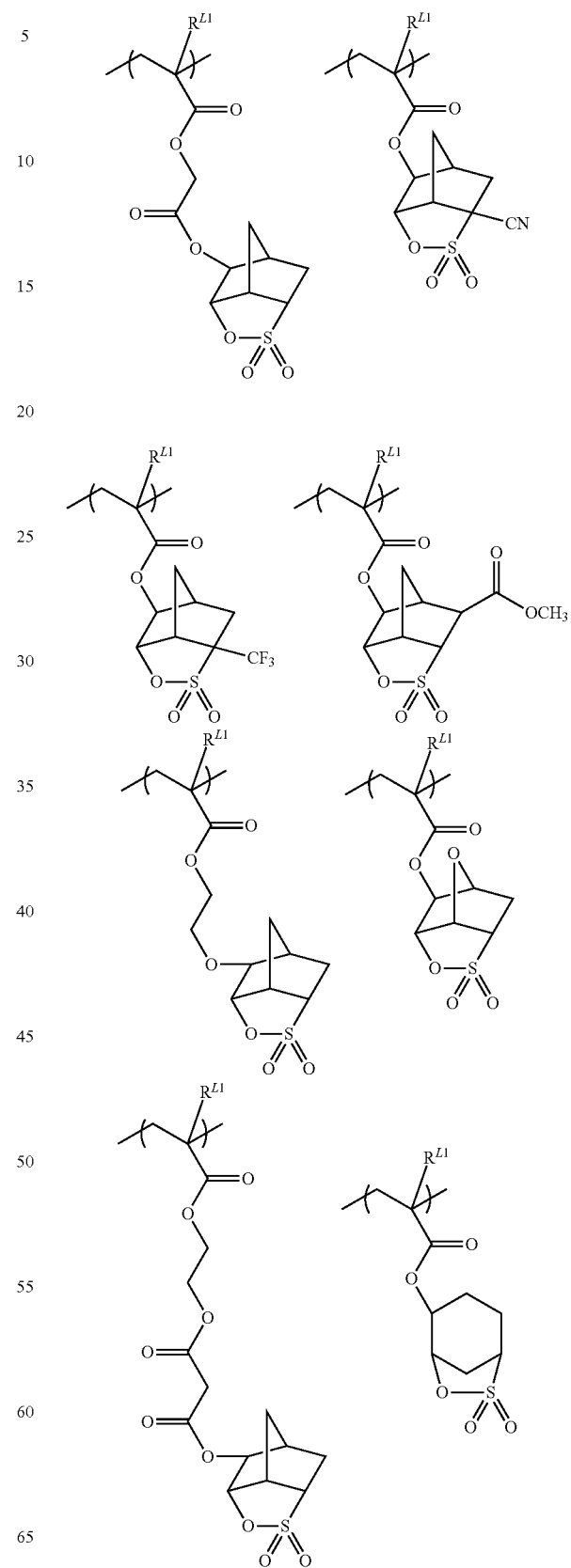

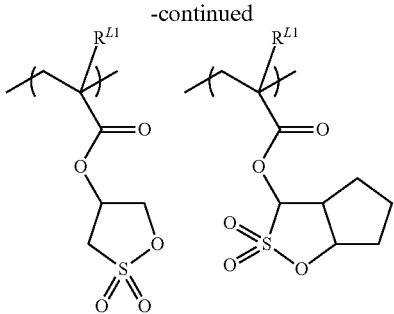

In the above formulae, $R^{L1}$ represents a hydrogen atom, a fluorine atom, a methyl group, or a trifluoromethyl group.

The structural unit (II) is preferably a structural unit including a lactone structure.

In the case in which the polymer (A) has the structural unit (II), the lower limit of a proportion of the structural unit (II) with respect to total structural units in the polymer (A) is preferably 5 mol %, more preferably 10 mol %, and still more preferably 15 mol %. The upper limit of the proportion is preferably 70 mol %, more preferably 65 mol %, and still more preferably 60 mol %.

Structural Unit (III)

The structural unit (III) is a structural unit including a phenolic hydroxyl group. The "phenolic hydroxyl group" as referred to herein is not limited to a hydroxy group directly bonding to a benzene ring, and means any hydroxy group directly bonding to an aromatic ring in general.

Due to further having the structural unit (III), the polymer (A) enables increasing the hydrophilicity of the resist film, whereby the solubility in the developer solution can be appropriately adjusted, and additionally, adhesiveness of the resist pattern to a substrate can be improved. Furthermore, in a case in which an extreme ultraviolet ray (EUV) or an electron beam is used as a radioactive ray employed for irradiation in an exposure step of the method of forming a resist pattern described later, the sensitivity to exposure light can be further improved. Therefore, the radiation-sensitive resin composition can be suitably used as a radiation-sensitive resin composition for exposure to an extreme ultraviolet ray or for exposure to an electron beam.

The structural unit (III) is exemplified by structural units represented by the following formulae, and the like.

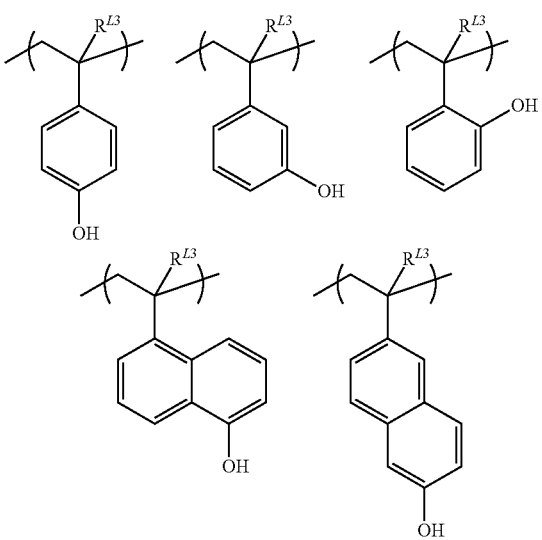

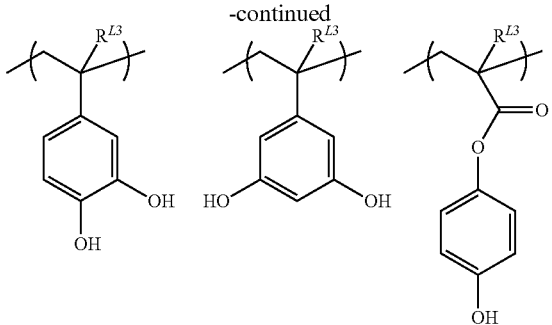

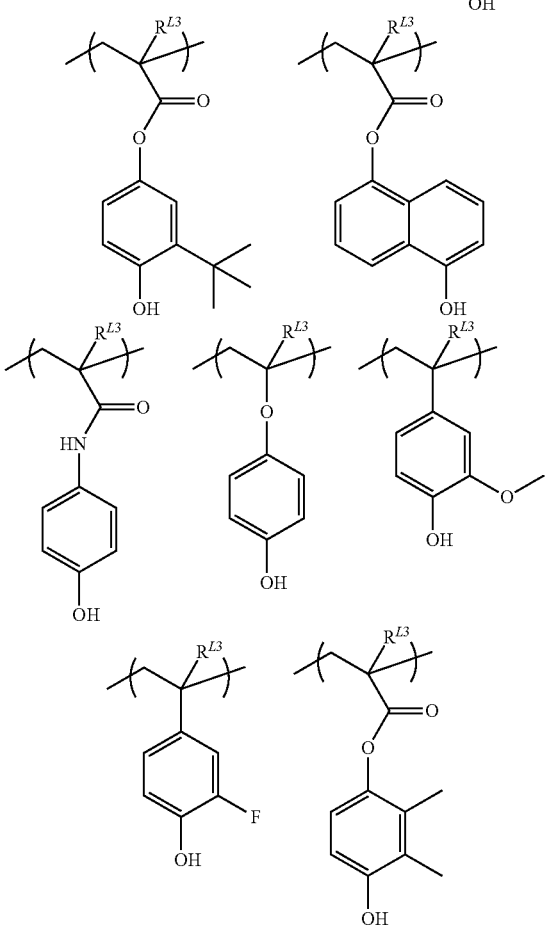

In the above formulae, $R^{L3}$ represents a hydrogen atom, a fluorine atom, a methyl group, or a trifluoromethyl group.

In the case in which the polymer (A) has the structural unit (III), the lower limit of a proportion of the structural unit (III) with respect to total structural units in the polymer (A) is preferably 20 mol %, and more preferably 30 mol %. The upper limit of the proportion is preferably 90 mol %, and more preferably 80 mol %.

Other Structural Unit(s)

The other structural unit(s) is/are exemplified by a structural unit (hereinafter, may be also referred to as "structural unit (IV)") including an alcoholic hydroxyl group; a structural unit other than the structural units (I) to (IV) (hereinafter, may be also referred to as "structural unit (V)") which includes an aromatic hydrocarbon group; and the like.

Examples of the structural unit (IV) include structural units represented by the following formulae, and the like.

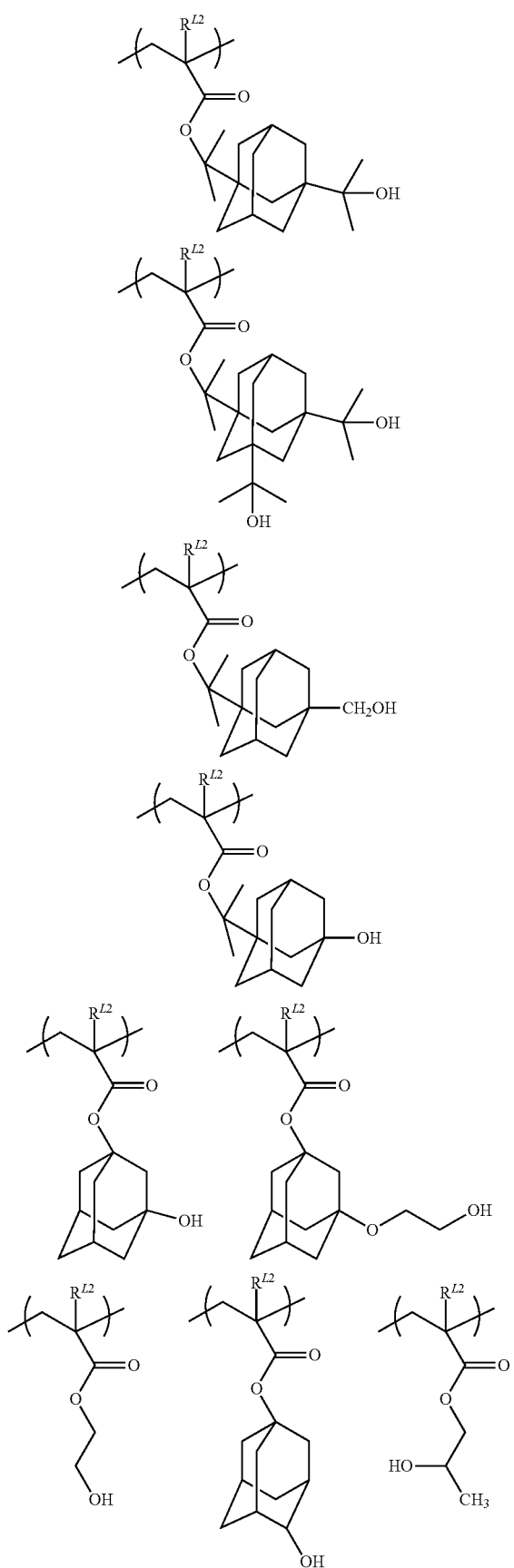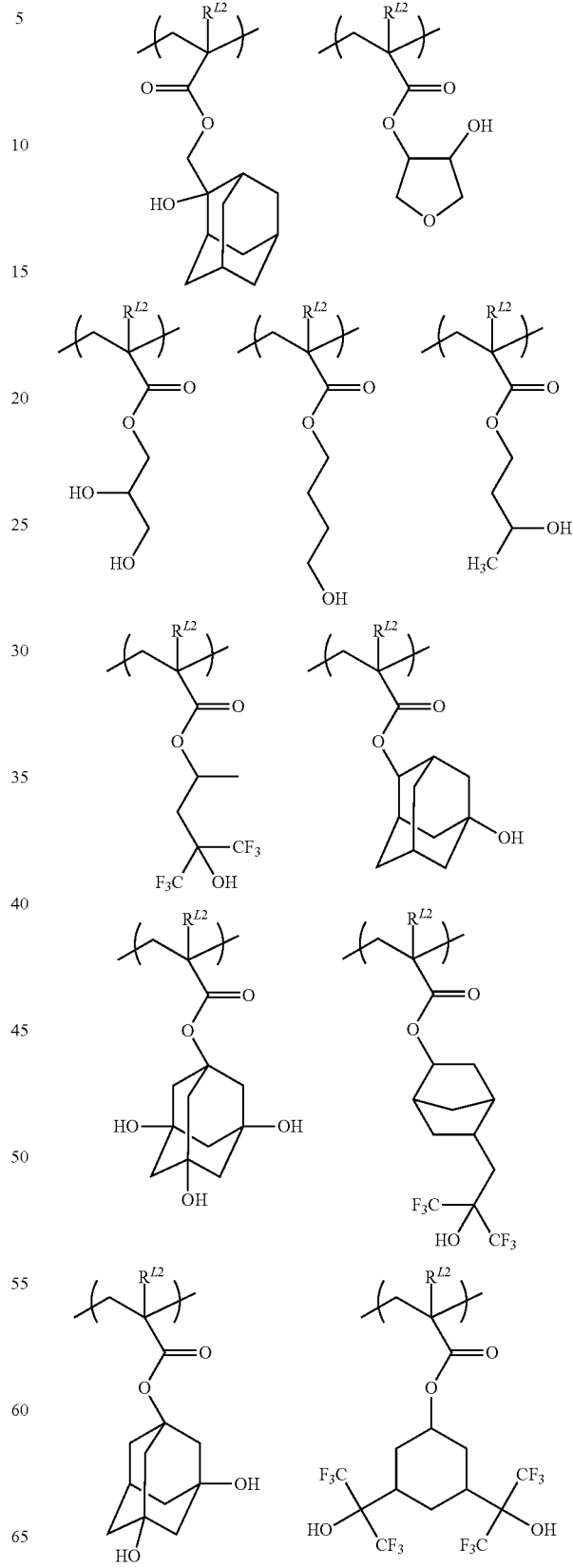

-continued

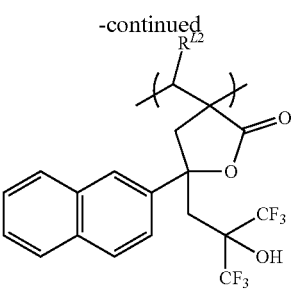

In the above formulae, $R^{L2}$ represents a hydrogen atom, a fluorine atom, a methyl group, or a trifluoromethyl group.

Examples of the monomer that gives the structural unit (V) include styrene, α-methylstyrene, 2-methylstyrene, 3-methylstyrene, 4-methylstyrene, phenyl (meth)acrylate, benzyl (meth)acrylate, 4-t-butylphenyl (meth)acrylate, acenaphthylene, 1-vinylnaphthalene, 2-vinylnaphthalene, 1-naphthyl (meth)acrylate, 2-naphthyl (meth)acrylate, 1-naphthylmethyl (meth)acrylate, 1-anthryl (meth)acrylate, 2-anthryl (meth)acrylate, 9-anthryl (meth)acrylate, 9-anthrylmethyl (meth)acrylate, 1-vinylpyrene, 2-vinylpyrene, and the like.

In the case in which the polymer (A) has the other structural unit(s), the lower limit of a proportion of the other structural unit(s) with respect to total structural units in the polymer (A) is preferably 1 mol %, and more preferably 5 mol %. The upper limit of the proportion is preferably 30 mol %, and more preferably 20 mol %.

The lower limit of a polystyrene-equivalent weight average molecular weight (Mw) of the polymer (A) as determined by gel permeation chromatography (GPC) is preferably 2,000, more preferably 3,000, and still more preferably 4,000. The upper limit of the Mw is preferably 10,000, more preferably 9,000, and still more preferably 8,000. When the Mw of the polymer (A) falls within the above range, the solubility in the developer solution can be appropriately adjusted.

The upper limit of a ratio (Mw/Mn, hereinafter may be also referred to as "dispersity index") of the Mw to a polystyrene-equivalent number average molecular weight (Mn) of the polymer (A) as determined by GPC is preferably 2.50, more preferably 2.00, and still more preferably 1.75. The lower limit of the ratio is typically 1.00, preferably 1.10, and more preferably 1.20. When the Mw/Mn of the polymer (A) falls within the above range, coating characteristics of the radiation-sensitive resin composition can be further improved.

As referred to herein, the Mw and Mn of the polymer are values measured by gel permeation chromatography (GPC) under the following conditions.

GPC columns: "G2000 HXL"×2, "G3000 HXL"×1, and "G4000 HXL"×1, available from Tosoh Corporation
   elution solvent: tetrahydrofuran
   flow rate: 1.0 mL/min
   sample concentration: 1.0% by mass
   amount of injected sample: 100 uL
   column temperature: 40° C.
   detector: differential refractometer
   standard substance: mono-dispersed polystyrene The lower limit of a proportion of the polymer (A) in the radiation-sensitive resin composition with respect to total components other than the organic solvent (D) is preferably 50% by mass, more preferably 60% by mass, still more preferably 70% by mass, and particularly preferably 80% by mass.

The polymer (A) can be synthesized by, for example, polymerizing a monomer that gives each structural unit according to a well-known procedure.

(B) Compound

The compound (B) is a compound represented by the following formula (1). The compound (B) is a substance which generates an acid upon irradiation with a radioactive ray, and functions as a radiation-sensitive acid generating agent in the radiation-sensitive resin composition. The radiation-sensitive resin composition may contain one, or two or more types of the compound (B).

Examples of the radioactive ray include: electromagnetic waves such as visible light rays, ultraviolet rays, far ultraviolet rays, extreme ultraviolet rays (EUV), X-rays, and γ-rays; charged particle rays such as electron beams and α-rays; and the like. A carboxy group and the like are generated by dissociation of the acid-labile group included in the structural unit (I) contained in the polymer (A) mediated by the acid generated from the compound (B), etc. upon irradiation with (exposure to) the radioactive ray to create a difference in solubility of the polymer (A) in a developer solution between the light-exposed regions and light-unexposed regions, thereby enabling formation of a resist pattern.

The lower limit of a temperature at which the acid dissociates the acid-labile group is preferably 80° C., more preferably 90° C., and still more preferably 100° C. The upper limit of the temperature is preferably 130° C., more preferably 120° C., and still more preferably 110° C. The lower limit of a time period of the acid dissociating the acid-labile group is preferably 10 sec, and more preferably 1 minute. The upper limit of the time period is preferably 10 min, and more preferably 2 min.

It is to be noted that herein below, a monovalent sulfonic acid anion represented by A⁻ in the following formula (1) may be also referred to as a "sulfonic acid anion," a part other than this sulfonic acid anion in the following formula (1) may be also referred to as an "onium cation," and a moiety represented by the following formula (2), described later, may be also referred to as the "group (X)."

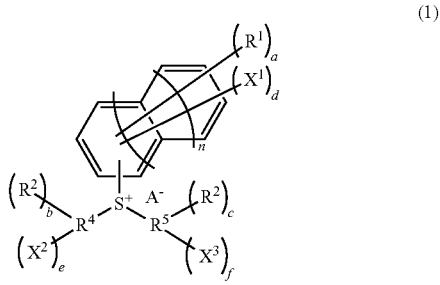

(1)

In the above formula (1), $R^1$, $R^2$, and $R^3$ each independently represent a halogen atom, a hydroxy group, a nitro group, or a monovalent organic group having 1 to 20 carbon atoms;

a is an integer of 0 to 7, wherein in a case in which a is no less than 2, a plurality of $R^1$s are identical or different from each other;

b is an integer of 0 to 4, wherein in a case in which b is no less than 2, a plurality of $R^2$s are identical or different from each other;

c is an integer of 0 to 4, wherein in a case in which c is no less than 2, a plurality of $R^1$s are identical or different from each other;

$X^1$, $X^2$, and $X^3$ each independently represent a group represented by formula (2), described later;

d is an integer of 0 to 7, wherein in a case in which d is no less than 2, a plurality of $X^1$s are identical or different from each other;

e is an integer of 0 to 4, wherein in a case in which e is no less than 2, a plurality of $X^2$s are identical or different from each other;

f is an integer of 0 to 4, wherein in a case in which f is no less than 2, a plurality of $X^3$s are identical or different from each other, wherein a sum of d, e, and f is no less than 1, a sum of a and d is no greater than 7, a sum of b and e is no greater than 4, and a sum of c and f is no greater than 4;

$R^4$ represents a hydrocarbon group having 1 to 20 carbon atoms and having a valency of (b+e+1) and $R^5$ represents a hydrocarbon group having 1 to 20 carbon atoms and having a valency of (c+f+1), or $R^4$ and $R^5$ taken together represent a heterocyclic structure having 4 to 20 ring atoms, together with the sulfur atom to which $R^4$ and $R^5$ bond;

n is 0 or 1; and $A^-$ represents a monovalent sulfonic acid anion.

The organic group having 1 to 20 carbon atoms which may be represented by $R^1$, $R^2$, or $R^3$ is exemplified by: a monovalent hydrocarbon group having 1 to 20 carbon atoms; a group (α') including a divalent heteroatom-containing group between two adjacent carbon atoms of the monovalent hydrocarbon group; a group (β') obtained by substituting with a monovalent heteroatom-containing group, a part or all of hydrogen atoms included in the monovalent hydrocarbon group or the group (α'); a group (γ') in which the monovalent hydrocarbon group, the group (α'), or the group (β') is combined with a divalent heteroatom-containing group; and the like.

Examples of the monovalent hydrocarbon group having 1 to 20 carbon atoms include groups similar to those exemplified as the monovalent hydrocarbon group having 1 to 20 carbon atoms which may be represented by $R^X$, $R^Y$, or $R^Z$ in the above formula (3), and the like.

Examples of the heteroatom that may constitute the monovalent or divalent heteroatom-containing group include heteroatoms similar to those exemplified as the heteroatom that may constitute the monovalent or divalent heteroatom-containing group in the divalent organic group having 1 to 20 carbon atoms which may be represented by $L^1$ in the above formula (3), and the like.

Examples of the divalent heteroatom-containing group include groups similar to those exemplified as the divalent heteroatom-containing group in the divalent organic group having 1 to 20 carbon atoms which may be represented by L in the above formula (3), and the like.

a is preferably 0 to 3, more preferably 0 to 2, and still more preferably 0 or 1. b is preferably 0 to 3, more preferably 0 to 2, and still more preferably 0 or 1. c is preferably 0 to 3, more preferably 0 to 2, and still more preferably 0 or 1.

Examples of the hydrocarbon group having 1 to 20 carbon atoms and having a valency of (b+e+1) which may be represented by $R^4$ include groups obtained by removing (b+e) hydrogen atoms from the groups exemplified as the monovalent hydrocarbon group having 1 to 20 carbon atoms which may be represented by $R^X$, $R^Y$, or $R^Z$ in the above formula (3), and the like.

Examples of the hydrocarbon group having 1 to 20 carbon atoms and having a valency (c+f+1) which may be represented by $R^5$ include groups obtained by removing (c+f) hydrogen atoms from the groups exemplified as the monovalent hydrocarbon group having 1 to 20 carbon atoms which may be represented by $R^X$, $R^Y$, or $R^Z$ in the above formula (3), and the like.

The heterocyclic structure having 4 to 20 ring atoms which may be represented by $R^4$ and $R^5$ taken together, together with the sulfur atom to which $R^4$ and $R^5$ bond, is exemplified by aliphatic heterocyclic structures such as a tetrahydrothiophene structure; aromatic heterocyclic structures such as a dibenzothiophene structure; and the like.

It is preferred that $R^4$ and $R^5$ each represent the aromatic heterocyclic structure, or that $R^4$ and $R^5$ taken together represent the heterocyclic structure having 4 to 20 ring atoms, together with the sulfur atom to which $R^4$ and $R^5$ bond.

d is preferably 0 to 3, and more preferably 0 to 2. e is preferably 0 to 3, and more preferably 0 to 2. f is preferably 0 to 2. A sum of d, e, and f is preferably no less than 1 and no greater than 4, more preferably no less than 1 and no greater than 3, and still more preferably 1 or 2.

n is preferably 0 or 1, and more preferably 0.

Group (X)

The group (X) is a group represented by the following formula (2). Due to the compound (B) having the group (X), introduction of substituents having a variety of functions is enabled without a loss of efficiency of generating the acid upon exposure. As a result, the radiation-sensitive resin composition enables forming a resist pattern with favorable sensitivity to exposure light and superiority in terms of the CDU performance and the LWR performance.

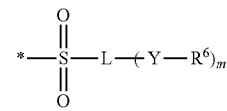

(2)

In the above formula (2),

L represents an organic group having 1 to 20 carbon atoms and having a valency of (m+1);

Y represents —COO—, —OCO—, or —N($R^7$)CO—, wherein $R^7$ represents a hydrogen atom or a monovalent hydrocarbon group having 1 to 20 carbon atoms;

$R^6$ represents a monovalent organic group having 1 to 20 carbon atoms;

m is an integer of 1 to 5, wherein in a case in which m is no less than 2, a plurality of Ys are identical or different and a plurality of $R^6$s are identical or different; and

* denotes a site of bonding to a part other than the group represented by the above formula (2) in the compound (B).

Examples of the organic group having 1 to 20 carbon atoms and having a valency of (m+1) represented by L include groups obtained by removing m hydrogen atoms from the groups exemplified as the monovalent organic group having 1 to 20 carbon atoms which may be represented by $R^1$, $R^2$, or $R^3$ in the above formula (1), and the like.

L represents preferably the hydrocarbon group having 1 to 20 carbon atoms and having a valency of (m+1). Examples of the hydrocarbon group having 1 to 20 carbon atoms and having a valency of (m+1) include groups obtained by removing m hydrogen atoms from the groups exemplified as the monovalent hydrocarbon group having 1 to 20 carbon atoms which may be represented by $R^X$, $R^Y$, or $R^Z$ in the above formula (3), and the like. More specifically, L represents preferably a group obtained by removing m hydrogen atoms from a methyl group, a group obtained by removing m hydrogen atoms from a tert-butyl group, a group obtained by removing m hydrogen atoms from a cyclohexyl group, or a group obtained by removing m hydrogen atoms from a phenyl group, and more preferably a group obtained by removing m hydrogen atoms from a methyl group, or a group obtained by removing m hydrogen atoms from a phenyl group.

Y represents preferably —COO— or —N($R^7$)CO—, and more preferably —COO— or —NHCO—. It is to be noted that when a site in Y that bonds with $R^6$ is denoted by "", Y represents preferably —COO—, —OCO—, or —N($R^7$)CO—.

m is preferably 1 to 4, and more preferably 1 to 3.

Examples of the monovalent organic group having 1 to 20 carbon atoms represented by $R^6$ include groups similar to those exemplified as the monovalent organic group having 1 to 20 carbon atoms which may be represented by $R^1$, $R^2$, or $R^3$ in the above formula (1), and the like. By means of appropriately selecting the monovalent organic group having 1 to 20 carbon atoms represented by $R^6$, introduction of substituents having a variety of functions, the substituents being, for example, an acid-labile group, a polar group, a halogen atom-containing group, and/or the like as explained later, is enabled without a loss of efficiency of generating the acid upon exposure.

$R^6$ represents preferably an acid-labile group (hereinafter, may be also referred to as "acid-labile group (x)"). It is to be noted that the "acid-labile group (x)" means a group that substitutes for a hydrogen atom in a carboxy group, and is dissociated by an action of an acid to give a carboxy group. In other words, in the case in which $R^6$ represents the acid-labile group (x), Y represents —COO—.

Examples of the acid-labile group (x) include a group (hereinafter, may be also referred to as "acid-labile group (x-1)") represented by the following formula (2-1), and the like.

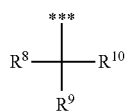

(2-1)

In the above formula (2-1), $R^8$ represents a hydrogen atom or a monovalent hydrocarbon group having 1 to 20 carbon atoms;

$R^9$ and $R^{10}$ each independently represent a monovalent hydrocarbon group having 1 to 20 carbon atoms, or $R^9$ and $R^{10}$ taken together represent an alicyclic structure having 3 to 20 ring atoms, together with the carbon atom to which $R^9$ and $R^{10}$ bond; and

*** denotes a site of bonding to Y in the above formula (2).

Examples of the monovalent hydrocarbon group having 1 to 20 carbon atoms which may be represented by $R^8$, $R^9$, or $R^{10}$ include groups similar to those exemplified as the monovalent hydrocarbon group having 1 to 20 carbon atoms which may be represented by $R^X$, $R^Y$, or $R^Z$ in the above formula (3), and the like.

Examples of the alicyclic structure having 3 to 20 ring atoms which may be represented by $R^9$ and $R^{10}$ taken together, together with the carbon atom to which $R^9$ and $R^{10}$ bond, include structures similar to those exemplified as the alicyclic structure having 3 to 20 ring atoms which may be represented by $R^Y$ and $R^Z$ taken together, together with the carbon atom to which $R^Y$ and $R^Z$ bond, in the above formula (3), and the like.

$R^8$ represents preferably the chain hydrocarbon group, and more preferably the alkyl group.

It is preferred that $R^9$ and $R^{10}$ each represent the chain hydrocarbon group, or that $R^9$ and $R^{10}$ taken together represent the saturated alicyclic structure, together with the carbon atom to which $R^9$ and $R^{10}$ bond.

The acid-labile group (x-1) is exemplified by groups represented by the following formulae (2-1-1) to (2-14), and the like.

(2-1-1)

(2-1-2)

(2-1-3)

(2-1-4)

In the above formulae (2-1-1) to (2-14), *** is as defined in the above formula (2-1).

Also preferable is that $R^6$ represents a lactone ring group, a sultone ring group, a carbonate ring group, an alcoholic hydroxyl group-containing alicyclic hydrocarbon group, a phenolic hydroxyl group-containing group, or an amide group (hereinafter, these may be also referred to as the "polar group"). Of these, $R^6$ represents further preferably the lactone ring group, the carbonate ring group, the alcoholic hydroxyl group-containing alicyclic hydrocarbon group, or the phenolic hydroxyl group-containing group.

Examples of the polar group include groups represented by the following formulae (2-2-1) to (2-2-4), and the like. It is to be noted that the group represented by the following formula (2-2-1) is a specific example of the lactone ring group, the group represented by the following formula (2-2-2) is a specific example of the carbonate ring group, the group represented by the following formula (2-2-3) is a specific example of the alcoholic hydroxyl group-containing alicyclic hydrocarbon group, and the group represented by the following formula (2-2-4) is a specific example of the phenolic hydroxyl group-containing group.

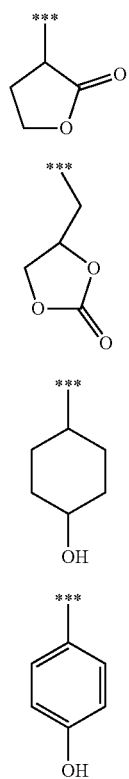

(2-2-1)

(2-2-2)

(2-2-3)

(2-2-4)

In the above formulae (2-2-1) to (2-2-4), *** is as defined in the above formula (2-1).

Also preferable is that $R^6$ represents a halogen atom-containing group. The halogen atom-containing group is exemplified by groups obtained by substituting with a halogen atom, a part or all of hydrogen atoms contained in the monovalent organic group having 1 to 20 atoms, and the like.

Examples of the halogen atom-containing group include groups represented by the following formulae (2-3-1) to (2-3-4), and the like.

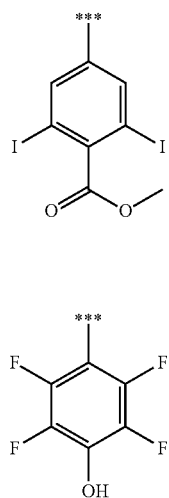

(2-3-1)

(2-3-2)

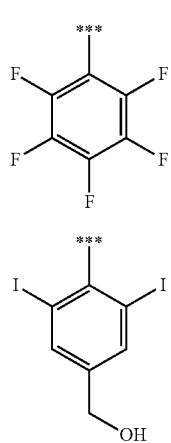

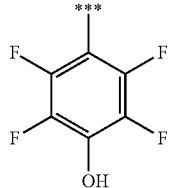

(2-3-3)

(2-3-4)

In the above formulae (2-3-1) to (2-3-4), *** is as defined in the above formula (2-1).

The onium cation is preferably a cation represented by, for example, one of the following formulae (1-1) to (1-15).

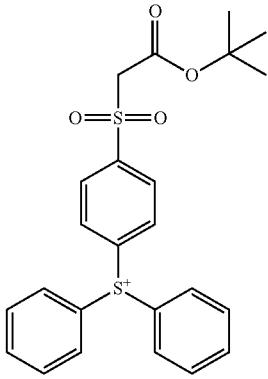

(1-1)

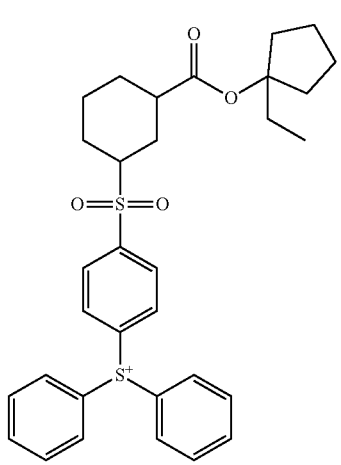

(1-2)

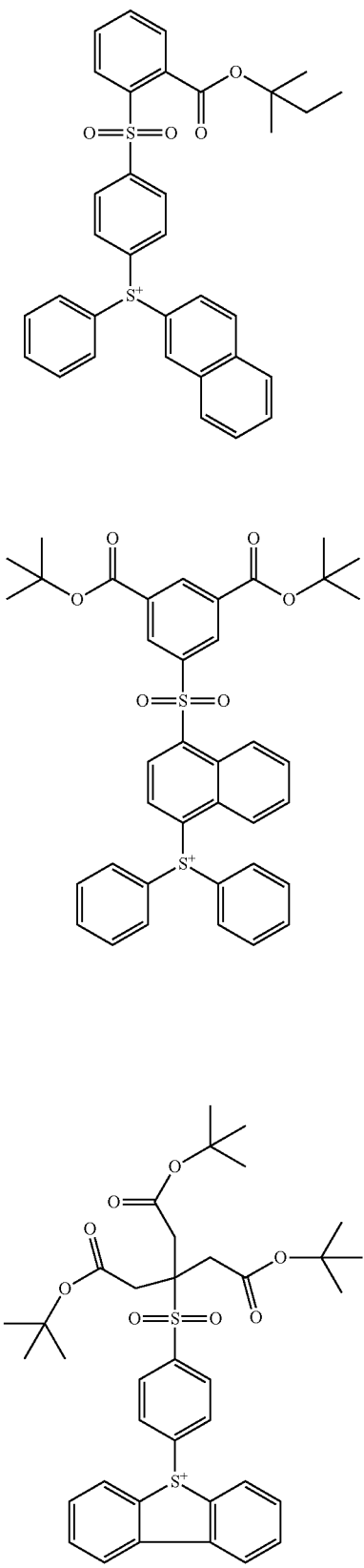
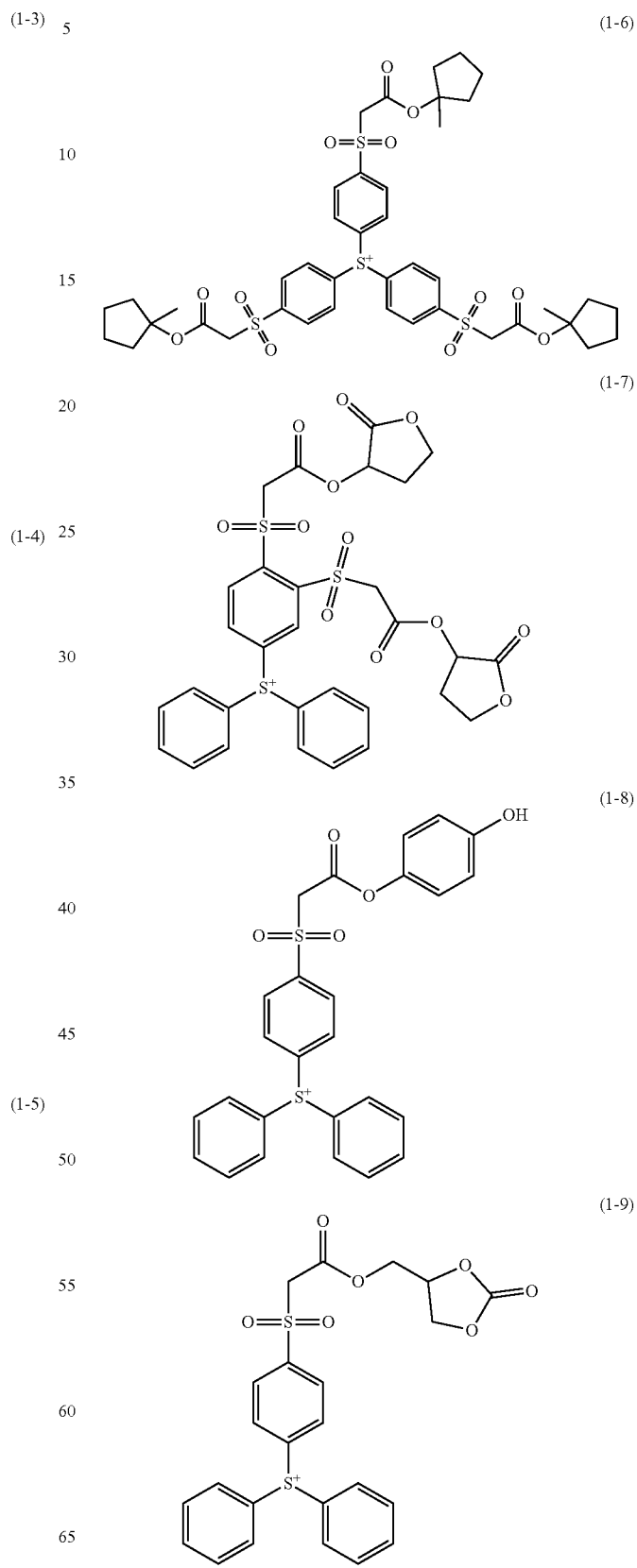

(1-10)
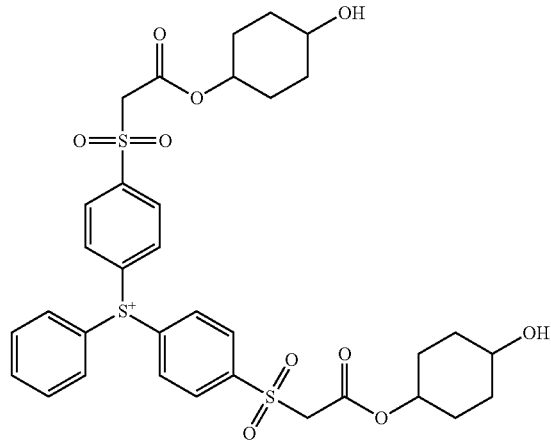
(1-11)
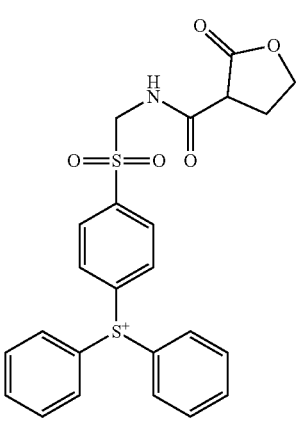
(1-12)
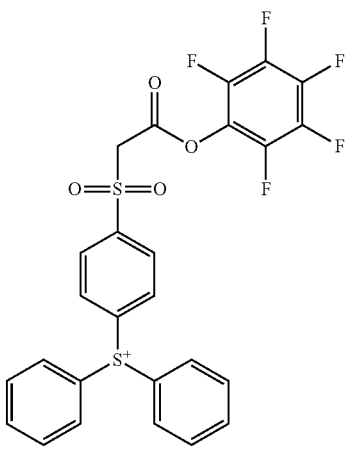
(1-13)
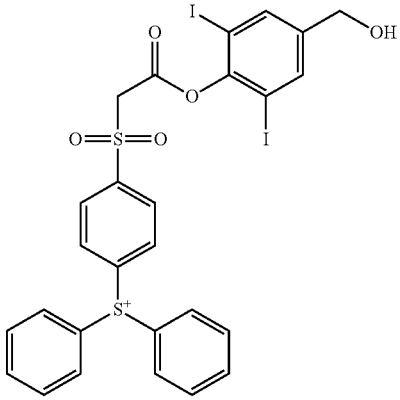
(1-14)
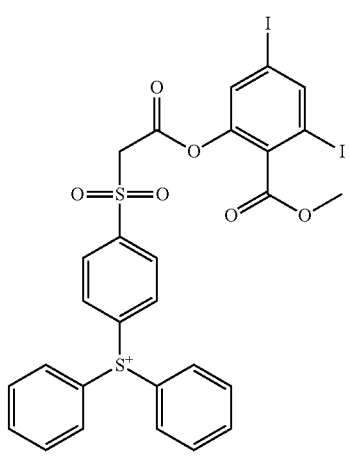
(1-15)
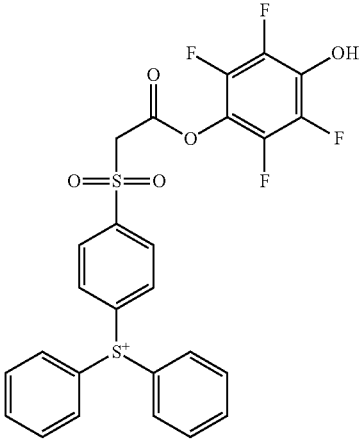
Sulfonic Acid Anion
The sulfonic acid anion represented by $A^-$ may be exemplified by a sulfonic acid anion (hereinafter, may be also referred to as "anion (X-1)") represented by the following formula (5), and the like.
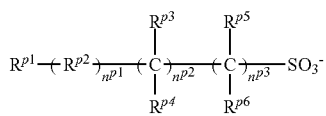
(5)

In the above formula (5), $R^{p1}$ represents a monovalent group including a ring structure having 5 or more ring atoms; $R^{p2}$ represents a divalent linking group; $R^{p3}$ and $R^{p4}$ each independently represent a hydrogen atom, a fluorine atom, a monovalent hydrocarbon group having 1 to 20 carbon atoms, or a monovalent fluorinated hydrocarbon group having 1 to 20 carbon atoms; $R^{p5}$ and $R^{p6}$ each independently represent a fluorine atom or a monovalent fluorinated hydrocarbon group having 1 to 20 carbon atoms; and $n^{p1}$ is an integer of 0 to 10, $n^{p2}$ is an integer of 0 to 10, and $n^{p3}$ is an integer of 0 to 10, wherein the sum of $n^{p1}$, $n^{p2}$ and $n^{p3}$ is no less than 1 and no greater than 30, and wherein in a case in which $n^{p1}$ is no less than 2, a plurality of $R^{p2}$s are identical or different from each other, in a case in which $n^{p2}$ is no less than 2, a plurality of $R^{p3}$s are identical or different from each other and a plurality of $R^{p4}$s are identical or different from each other, and in a case in which $n^{p3}$ is no less than 2, a plurality of $R^{p5}$s are identical or different from each other and a plurality of $R^{p6}$s are identical or different from each other.

The monovalent group including a ring structure having 5 or more ring atoms which is represented by $R^{p1}$ is exemplified by: a monovalent group including an alicyclic structure having 5 or more ring atoms; a monovalent group including an aliphatic heterocyclic structure having 5 or more ring atoms; a monovalent group including an aromatic carbocyclic structure having 5 or more ring atoms; a monovalent group including an aromatic heterocyclic structure having 5 or more ring atoms; and the like.

Examples of the alicyclic structure having 5 or more ring atoms include: monocyclic saturated alicyclic structures such as a cyclopentane structure, a cyclohexane structure, a cycloheptane structure, a cyclooctane structure, a cyclononane structure, a cyclodecane structure, and a cyclododecane structure; monocyclic unsaturated alicyclic structures such as a cyclopentene structure, a cyclohexene structure, a cycloheptene structure, a cyclooctene structure, and a cyclodecene structure; polycyclic saturated alicyclic structures such as a norbornane structure, an adamantane structure, a tricyclodecane structure, and a tetracyclododecane structure; polycyclic unsaturated alicyclic structures such as a norbornene structure and a tricyclodecene structure; and the like.

Examples of the aliphatic heterocyclic structure having 5 or more ring atoms include: lactone structures such as a hexanolactone structure and a norbornanelactone structure; sultone structures such as a hexanosultone structure and a norbornanesultone structure; oxygen atom-containing heterocyclic structures such as an oxacycloheptane structure and an oxanorbornane structure; nitrogen atom-containing heterocyclic structures such as an azacyclohexane structure and a diazabicyclooctane structure; sulfur atom-containing heterocyclic structures such as a thiacyclohexane structure and a thianorbornane structure; and the like.

Examples of the aromatic carbocyclic structure having 5 or more ring atoms include a benzene structure, a naphthalene structure, a phenanthrene structure, an anthracene structure, and the like.

Examples of the aromatic heterocyclic structure having 5 or more ring atoms include: oxygen atom-containing heterocyclic structures such as a furan structure, a pyran structure, a benzofuran structure, and a benzopyran structure; nitrogen atom-containing heterocyclic structures such as a pyridine structure, a pyrimidine structure, and an indole structure; and the like.

The lower limit of the number of ring atoms in the ring structure in $R^{p1}$ is preferably 6, more preferably 8, still more preferably 9, and particularly preferably 10. The upper limit of the number of ring atoms is preferably 15, more preferably 14, still more preferably 13, and particularly preferably 12. When the number of ring atoms falls within the above range, the diffusion length of the acid can be further properly decreased, and as a result, the sensitivity to exposure light as well as the LWR performance of the resist pattern formed from the radiation-sensitive resin composition can be further improved, whereby a process window can be further expanded.

A part or all of hydrogen atoms included in the ring structure of $R^{p1}$ may be substituted with a substituent. Examples of the substituent include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like. Of these, a hydroxy group is preferred.

$R^{p1}$ represents preferably a monovalent group including an alicyclic structure having 5 or more ring atoms, a monovalent group including an alicyclic heterocyclic structure having 5 or more ring atoms, or a monovalent group including an aromatic ring structure having 5 or more ring atoms, and more preferably a monovalent group including a polycyclic saturated alicyclic structure having 5 or more ring atoms, a monovalent group including an oxygen atom-containing heterocyclic structure having 5 or more ring atoms, or a monovalent group including a sulfur atom-containing heterocyclic structure having 5 or more ring atoms.

Examples of the divalent linking group represented by $R^{p2}$ include a carbonyl group, an ether group, a carbonyloxy group, a sulfide group, a thiocarbonyl group, a sulfonyl group, a divalent hydrocarbon group, and the like. Of these, the carbonyloxy group, the sulfonyl group, an alkanediyl group, or a divalent alicyclic saturated hydrocarbon group is preferred, and the carbonyloxy group is more preferred.

The monovalent hydrocarbon group having 1 to 20 carbon atoms which may be represented by each of $R^{p3}$ and $R^{p4}$ is exemplified by an alkyl group having 1 to 20 carbon atoms, and the like. The monovalent fluorinated hydrocarbon group having 1 to 20 carbon atoms which may be represented by each of $R^{p3}$ and $R^{p4}$ is exemplified by a fluorinated alkyl group having 1 to 20 carbon atoms, and the like. $R^{p3}$ and $R^{p4}$ each independently represent preferably a hydrogen atom, a fluorine atom, or a fluorinated alkyl group, more preferably a hydrogen atom, a fluorine atom, or a perfluoroalkyl group, and still more preferably a hydrogen atom, a fluorine atom, or a trifluoromethyl group.

The monovalent fluorinated hydrocarbon group having 1 to 20 carbon atoms which may be represented by each of $R^{p5}$ and $R^{p6}$ is exemplified by a fluorinated alkyl group having 1 to 20 carbon atoms, and the like. $R^{p5}$ and $R^{p6}$ each independently represent preferably a fluorine atom or a fluorinated alkyl group, more preferably a fluorine atom or a perfluoroalkyl group, still more preferably a fluorine atom or a trifluoromethyl group, and particularly preferably a fluorine atom.

$n^{p1}$ is preferably 0 to 5, more preferably 0 to 2, and still more preferably 0 or 1.

$n^{p2}$ is preferably 0 to 5, more preferably 0 to 2, and still more preferably 0 or 1.

The lower limit of $n^{p3}$ is preferably 1, and more preferably 2. When $n^{p3}$ is no less than 1, strength of the acid can be enhanced. The upper limit of $n^{p3}$ is preferably 4, more preferably 3, and still more preferably 2.

The lower limit of a sum of $n^{p1}$, $n^{p2}$, and $n^{p3}$ is preferably 2, and more preferably 4. The upper limit of the sum of $n^{p1}$, $n^{p2}$, and $n^{p3}$ is preferably 20, and more preferably 10.
Examples of the anion (X-1) include anions (hereinafter, may be also referred to as "anion (X-1-1) to (X-1-16)") represented by the following formulae (5-1) to (5-16), and the like.
(5-1)
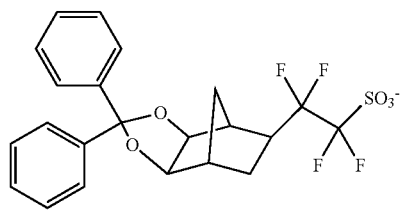
(5-2)
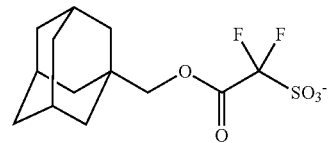
(5-3)
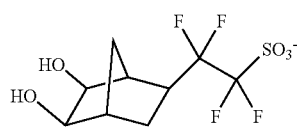
(5-4)
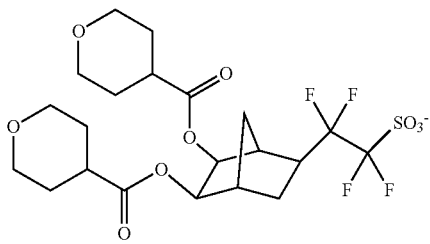
(5-5)
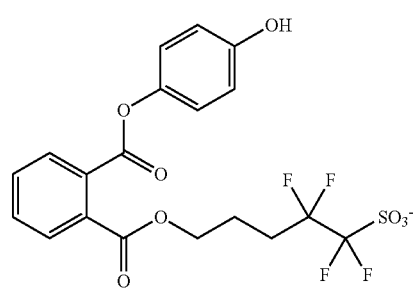
(5-6)
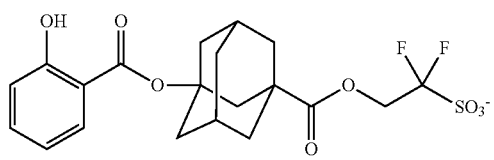
-continued
(5-7)
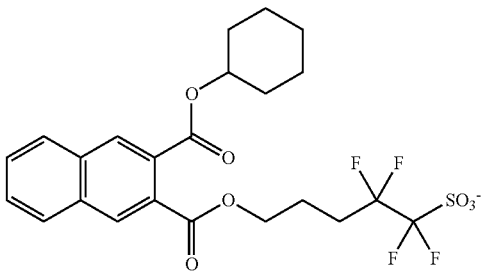
(5-8)
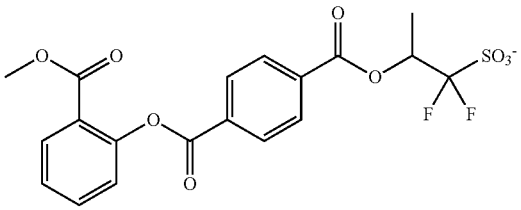
(5-9)
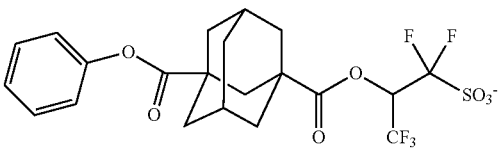
(5-10)
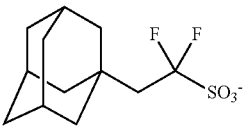
(5-11)
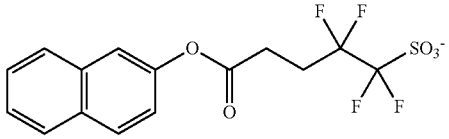
(5-12)
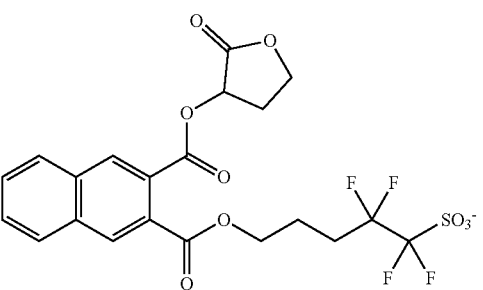
(5-13)
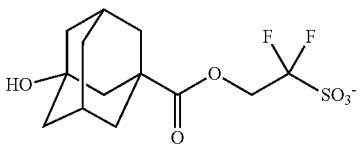

-continued (5-14)

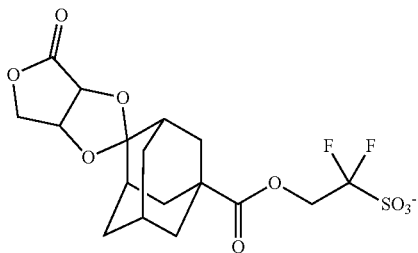

(5-15)

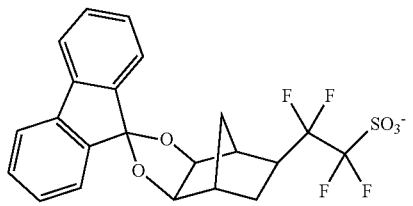

(5-16)

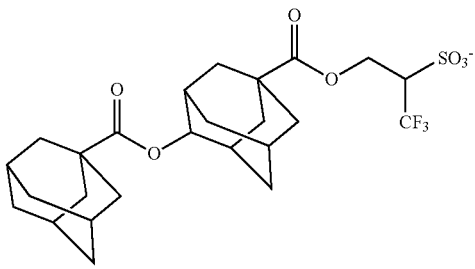

As the compound (B), a compound in which the onium cation and the sulfonic acid anion are appropriately combined can be used.

The lower limit of a content of the compound (B) in the radiation-sensitive resin composition with respect to 100 parts by mass of the polymer (A) is preferably 0.1 parts by mass, more preferably 1 part by mass, and still more preferably 5 parts by mass. The upper limit of the content is preferably 80 parts by mass, more preferably 70 parts by mass, and still more preferably 60 parts by mass. When the content of the compound (B) falls within the above range, the sensitivity to exposure light, as well as the CDU performance and the LWR performance of the resist pattern formed from the radiation-sensitive resin composition can be further improved.

(C) Acid Diffusion Control Agent

The acid diffusion control agent (C) is able to control a diffusion phenomenon, in the resist film, of the acid generated from the compound (B), etc. upon exposure, thereby serving to inhibit unwanted chemical reactions in light-unexposed regions. When the radiation-sensitive resin composition contains the acid diffusion control agent (C), the sensitivity to exposure light, as well as the CDU performance and the LWR performance resulting from the radiation-sensitive resin composition can be further improved. The radiation-sensitive resin composition may contain one, or two or more types of the acid diffusion control agent (C).

The acid diffusion control agent (C) is exemplified by a nitrogen atom-containing compound, a photodegradable base that is photosensitized by exposure to generate a weak acid, and the like.

Examples of the nitrogen atom-containing compound include: amine compounds such as tripentylamine and trioctylamine; amide group-containing compounds such as formamide and N,N-dimethylacetamide; urea compounds such as urea and 1,1-dimethylurea; nitrogen-containing heterocyclic compounds such as pyridine, N-(undecylcarbonyloxyethyl)morpholine, and N-t-pentyloxycarbonyl-4-hydroxypiperidine; and the like.

The photodegradable base is exemplified by a compound containing an onium cation degraded by exposure, and an anion of a weak acid; and the like. In a light-exposed region, the photodegradable base generates a weak acid from: a proton produced upon degradation of the onium cation; and the anion of the weak acid, whereby acid diffusion controllability decreases.

Examples of the onium cation degraded by exposure include a triphenylsulfonium cation, a phenyldibenzothiophenium cation, a diphenyl(4-(cyclohexylsulfonyl)phenyl)sulfonium cation, a tris(4-fluorophenyl)sulfonium cation, and the like.

Examples of the anion of the weak acid include anions represented by the following formulae, and the like.

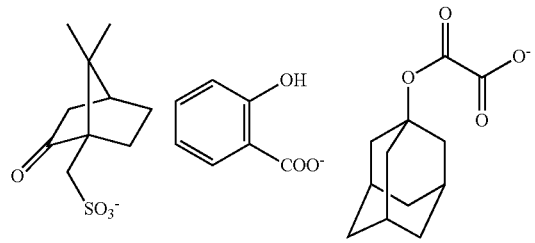

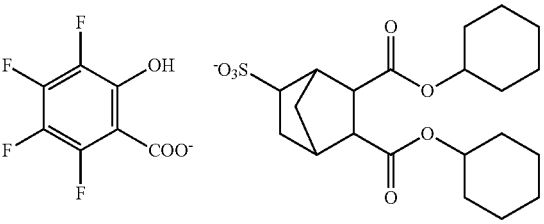

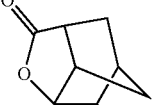

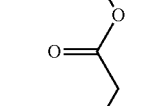

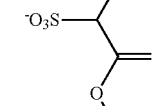

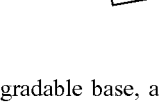

As the photodegradable base, a compound in which the onium cation degraded by exposure and the anion of a weak acid are appropriately combined can be used.

In the case of the radiation-sensitive resin composition containing the acid diffusion control agent (C), the lower limit of a content of the acid diffusion control agent (C) with respect to 100 parts by mass of the polymer (A) is preferably 0.5 parts by mass, more preferably 1 part by mass, and still more preferably 3 parts by mass. The upper limit of the content is preferably 40 parts by mass, more preferably 30 parts by mass, and still more preferably 25 parts by mass. When the content of the acid diffusion control agent (C) falls within the above range, the sensitivity to exposure light, as well as the CDU performance and the LWR performance of the resist pattern formed from the radiation-sensitive resin composition can be further improved.

(D) Organic Solvent

The radiation-sensitive resin composition typically contains the organic solvent (D). The organic solvent (D) is not particularly limited as long as it is a solvent capable of dissolving or dispersing at least the polymer (A) and the compound (B), as well as the acid diffusion control agent (C), the other optional component(s), and the like, which is/are contained as needed.

The organic solvent (D) is exemplified by an alcohol solvent, an ether solvent, a ketone solvent, an amide solvent, an ester solvent, a hydrocarbon solvent, and the like. The radiation-sensitive resin composition may contain one, or two or more types of the organic solvent (D).

Examples of the alcohol solvent include:
aliphatic monohydric alcohol solvents having 1 to 18 carbon atoms such as 4-methyl-2-pentanol and n-hexanol;
alicyclic monohydric alcohol solvents having 3 to 18 carbon atoms such as cyclohexanol;
polyhydric alcohol solvents having 2 to 18 carbon atoms such as 1,2-propylene glycol;
polyhydric alcohol partial ether solvents having 3 to 19 carbon atoms such as propylene glycol 1-monomethyl ether; and the like.

Examples of the ether solvent include:
dialkyl ether solvents such as diethyl ether, dipropyl ether, dibutyl ether, dipentyl ether, diisoamyl ether, dihexyl ether, and diheptyl ether;
cyclic ether solvents such as tetrahydrofuran and tetrahydropyran;
aromatic ring-containing ether solvents such as diphenyl ether and anisole; and the like.

Examples of the ketone solvent include:
chain ketone solvents such as acetone, methyl ethyl ketone, methyl n-propyl ketone, methyl n-butyl ketone, diethyl ketone, methyl iso-butyl ketone, 2-heptanone, ethyl n-butyl ketone, methyl n-hexyl ketone, di-iso-butyl ketone, and trimethylnonanone;
cyclic ketone solvents such as cyclopentanone, cyclohexanone, cycloheptanone, cyclooctanone, and methylcyclohexanone;
2,4-pentanedione, acetonylacetone, and acetophenone; and the like.

Examples of the amide solvent include:
cyclic amide solvents such as N,N'-dimethylimidazolidinone and N-methylpyrrolidone;
chain amide solvents such as N-methylformamide, N,N-dimethylformamide, N,N-diethylformamide, acetamide, N-methylacetamide, N,N-dimethylacetamide, and N-methylpropionamide; and the like.

Examples of the ester solvent include:
monocarboxylic acid ester solvents such as n-butyl acetate and ethyl lactate;
lactone solvents such as γ-butyrolactone and valerolactone;
polyhydric alcohol carboxylate solvents such as propylene glycol acetate;
polyhydric alcohol partial ether carboxylate solvents such as propylene glycol monomethyl ether acetate;
polyhydric carboxylic acid diester solvents such as diethyl oxalate;
carbonate solvents such as dimethyl carbonate and diethyl carbonate; and the like.

Examples of the hydrocarbon solvent include:
aliphatic hydrocarbon solvents having 5 to 12 carbon atoms such as n-pentane and n-hexane;
aromatic hydrocarbon solvents having 6 to 16 carbon atoms such as toluene and xylene; and the like.

The organic solvent (D) is preferably the alcohol solvent and/or the ester solvent, more preferably the polyhydric alcohol partial ether solvent having 3 to 19 carbon atoms and/or the polyhydric alcohol partial ether carboxylate solvent, and still more preferably propylene glycol 1-monomethyl ether and/or propylene glycol 1-monomethyl ether acetate.

In the case of the radiation-sensitive resin composition containing the organic solvent (D), the lower limit of a proportion of the organic solvent (D) with respect to total components contained in the radiation-sensitive resin composition is preferably 50% by mass, more preferably 60% by mass, still more preferably 70% by mass, and particularly preferably 80% by mass. The upper limit of the proportion is preferably 99.9% by mass, more preferably 99.5% by mass, and still more preferably 99.0% by mass.

(E) Polymer

The polymer (E) is a polymer having a percentage content by mass of fluorine atoms greater than that of the polymer (A). In general, a polymer being more hydrophobic than the polymer which is to be a base polymer tends to be localized in a surface layer of the resist film. Since the polymer (E) has a percentage content by mass of fluorine atoms greater than that of the polymer (A), the polymer (E) tends to be localized in a surface layer of the resist film due to the characteristic resulting from the hydrophobicity. As a result, in the case in which the radiation-sensitive resin composition contains the polymer (E), elution of the acid generating agent, the acid diffusion control agent, and the like into a liquid immersion medium can be inhibited during the liquid immersion lithography. In addition, in the case in which the radiation-sensitive resin composition contains the polymer (E), an advancing contact angle of a liquid immersion medium on the resist film can be adjusted to fall within a desired range owing to the hydrophobicity that results from the characteristics of the polymer (E), thereby enabling generation of the bubble defects to be inhibited. Furthermore, the radiation-sensitive resin composition leads to an increase in a receding contact angle of the liquid immersion medium on the resist film, whereby a scanning exposure at a high speed without being accompanied by residual water droplets is enabled. Due to further containing the polymer (E) in this manner, the radiation-sensitive resin composition is capable of forming a resist film suited for a liquid immersion lithography process. Furthermore, due to containing the polymer (E), the radiation-sensitive resin composition can form a resist pattern with generation of defects being inhibited.

The lower limit of a percentage content by mass of fluorine atoms in the polymer (E) is preferably 1% by mass, more preferably 2% by mass, and still more preferably 3% by mass. The upper limit of the percentage content by mass is preferably 60% by mass, more preferably 50% by mass, and still more preferably 40% by mass. When the percentage content by mass of fluorine atoms falls within the above range, localization of the polymer (E) in the resist film can be more adequately adjusted. It is to be noted that the percentage content by mass of fluorine atoms in the polymer may be calculated based on the structure of the polymer determined by $^{13}$C-NMR spectroscopy.

The mode of incorporation of the fluorine atom in the polymer (E) is not particularly limited, and the fluorine atom may be bonded to either the main chain or the side chain of the polymer (E). In a preferred mode of incorporation of the fluorine atom in the polymer (E), the polymer (E) has a structural unit (hereinafter, may be also referred to as "structural unit (I')") including a fluorine atom. The polymer (E) may further have a structural unit aside from the structural unit (I'). The polymer (E) may have one, or two or more types of each structural unit. The radiation-sensitive resin composition may contain one, or two or more types of the polymer (E).

Each structural unit contained in the polymer (E) is described below.

Structural Unit (I')

The structural unit (I') is a structural unit including a fluorine atom. Examples of the structural unit (I') include a structural unit (hereinafter, may be also referred to as "structural unit (I'-1)") represented by the following formula (f), and the like.

(f)

In the above formula (f), $R^{f1}$ represents a hydrogen atom, a fluorine atom, a methyl group, or a trifluoromethyl group;

$L^2$ represents a single bond, an oxygen atom, a sulfur atom, —COO—, —SO$_2$NH—, —CONH—, or —OCONH—; and $R^{f2}$ represents a monovalent organic group having 1 to 10 carbon atoms including a fluorine atom.

In light of the copolymerizability of a monomer that gives the structural unit (I'-1), $R^{f1}$ represents preferably a hydrogen atom or a methyl group, and more preferably a methyl group.

$L^2$ represents preferably —COO—.

Examples of the monovalent organic group having 1 to 10 carbon atoms including a fluorine atom represented by $R^{f2}$ include groups similar to those exemplified as the monovalent organic group having 1 to 20 carbon atoms which may be represented by $R^1$, $R^2$ or $R^3$ in the above formula (1), and the like.

$R^{f2}$ represents preferably a fluorinated chain hydrocarbon group or a group obtained by substituting with a hydroxy group, a part or all of hydrogen atoms of the fluorinated chain hydrocarbon group.

The structural unit (I'-1) is preferably one of structural units represented by the following formulae.

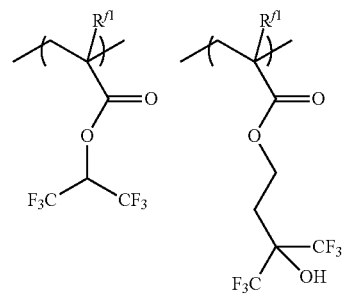

In the above formulae, $R^{f1}$ is as defined in the above formula (f).

In the case in which the polymer (E) has the structural unit (I'), the lower limit of a proportion of the structural unit (I') with respect to the total structural units constituting the polymer (E) is preferably 20 mol %, more preferably 30 mol %, and still more preferably 40 mol %. The upper limit of the proportion is preferably 90 mol %, more preferably 80 mol %, and still more preferably 70 mol %. When the proportion of the structural unit (F) falls within the above range, the percentage content by mass of the fluorine atoms in the polymer (E) can be more properly adjusted.

Other Structural Unit

Examples of the other structural unit include a structural unit (hereinafter, may be also referred to as "structural unit (II')") having an acid-labile group, and the like. Examples of the structural unit (II') include structural units similar to those exemplified as the structural unit (I) of the polymer (A), and the like.

In the case in which the polymer (E) has the structural unit (II'), the lower limit of a proportion of the structural unit (II') with respect to the total structural units constituting the polymer (E) is preferably 10 mol %, more preferably 20 mol %, and still more preferably 30 mol %. The upper limit of the proportion is preferably 80 mol %, more preferably 70 mol %, and still more preferably 60 mol %.

The lower limit of the Mw of the polymer (E) as determined by GPC is preferably 1,000, more preferably 2,000, still more preferably 3,000, and particularly preferably 4,000. The upper limit of the Mw is preferably 50,000, more preferably 20,000, still more preferably 10,000, and particularly preferably 8,000.

The upper limit of the ratio (Mw/Mn) of the Mw to the Mn of the polymer (E) as determined by GPC is preferably 5.00, more preferably 3.00, still more preferably 2.50, and particularly preferably 2.00. The lower limit of the ratio is typically 1.00, and preferably 1.20.

The polymer (E) can be synthesized similarly to the polymer (A), for example, by polymerizing a monomer that gives each structural unit according to a well-known procedure.

In the case in which the radiation-sensitive resin composition contains the polymer (E), the lower limit of a content of the polymer (E) with respect to 100 parts by mass of the polymer (A) is preferably 0.5 parts by mass, more preferably 1 part by mass, and still more preferably 5 parts by mass. The upper limit of the content is preferably 20 parts by mass, more preferably 15 parts by mass, and still more preferably 10 parts by mass.

Other Optional Component(s)

The other optional component(s) is/are exemplified by an acid generating agent (hereinafter, may be also referred to as "other acid generating agent") other than the compound (B), a surfactant, and the like. The radiation-sensitive resin composition may contain one, or two or more types each of the other optional component(s).

The other acid generating agent may be exemplified by an onium salt compound, an N-sulfonyloxyimide compound, a sulfonimide compound, a halogen-containing compound, a diazoketone compound, and the like.

Examples of the onium salt compound include sulfonium salts, tetrahydrothiophenium salts, iodonium salts, phosphonium salts, diazonium salts, pyridinium salts, and the like.

Specific examples of the other acid generating agent include compounds disclosed in paragraphs [0080] to [0113] of Japanese Unexamined Patent Application, Publication No. 2009-134088, and the like.

In the case in which the radiation-sensitive resin composition contains the other acid generating agent, the lower limit of a content of the other acid generating agent in the radiation-sensitive resin composition with respect to 100 parts by mass of the polymer (A) is preferably 0.1 parts by mass, and more preferably 1 part by mass. The upper limit of the content is preferably 30 parts by mass, and more preferably 20 parts by mass.

Method of Preparing Radiation-Sensitive Resin Composition

The radiation-sensitive resin composition may be prepared, for example, by: mixing the polymer (A) and the compound (B), as well the acid diffusion control agent (C), the organic solvent (D), the polymer (E), and the other optional component(s), and the like, which are added as needed, in a certain ratio; and preferably filtering a thus resulting mixture through a membrane filter having a pore size of no greater than 0.2 μm.

Method of Forming Resist Pattern

The method of forming a resist pattern according to another embodiment of the present invention includes: a step (hereinafter, may be also referred to as "applying step") of applying a radiation-sensitive resin composition directly or indirectly on a substrate; a step (hereinafter, may be also referred to as "exposing step") of exposing a resist film formed by the applying step; and a step (hereinafter, may be also referred to as "developing step") of developing the resist film exposed. In the applying step of the method of forming a resist pattern, the radiation-sensitive resin composition of the one embodiment of the present invention is used as the radiation-sensitive resin composition.

According to the method of forming a resist film, due to using the radiation-sensitive resin composition of the one embodiment of the present invention as the radiation-sensitive resin composition in the applying step, formation of a resist pattern with favorable sensitivity to exposure light and superiority in terms of the CDU performance and the LWR performance is enabled.

Each step included in the method of forming a resist pattern will be described below.

Applying Step

In this step, the radiation-sensitive resin composition is applied directly or indirectly on the substrate. By this step, the resist pattern is formed directly or indirectly on the substrate.

In this step, the radiation-sensitive resin composition of the one embodiment of the present invention, described above, is used as the radiation-sensitive resin composition.

The substrate is exemplified by a conventionally well-known substrate such as a silicon wafer, a wafer coated with silicon dioxide or aluminum, and the like. In addition, the case of the radiation-sensitive resin composition being applied indirectly on the substrate is exemplified by a case of the radiation-sensitive resin composition being applied on an antireflective film formed on the substrate, and the like. Examples of such an antireflective film include an organic or inorganic antireflective film disclosed in Japanese Examined Patent Application, Publication No. H6-12452, Japanese Unexamined Patent Application, Publication No. S59-93448, and the like.

An application procedure is exemplified by spin coating, cast coating, roll coating, and the like. After the application, soft baking (hereinafter, may be also referred to as "SB" or "prebaking (PB)")) may be carried out as needed for evaporating the solvent remaining in the coating film. The lower limit of a SB temperature is preferably 60° C., and more preferably 80° C. The upper limit of the SB temperature is preferably 150° C., and more preferably 140° C. The lower limit of a SB time period is preferably 5 sec, and more preferably 10 sec. The upper limit of the SB time period is preferably 600 sec, and more preferably 300 sec. The lower limit of an average thickness of the resist film formed is preferably 10 nm, and more preferably 20 nm. The upper limit of the average thickness is preferably 1,000 nm, and more preferably 500 nm.

Exposing Step

In this step, the resist film formed by the applying step is exposed. This exposure is carried out by irradiation with an exposure light through a photomask (as the case may be, through a liquid immersion medium such as water). Examples of the exposure light include electromagnetic waves such as visible light rays, ultraviolet rays, far ultraviolet rays, extreme ultraviolet rays (EUV), X-rays and γ-rays; charged particle rays such as electron beams and α-rays; and the like, which may be selected in accordance with a line width and the like of the intended pattern. Of these, far ultraviolet rays, EUV, or electron beams are preferred; an ArF excimer laser beam (wavelength: 193 nm), a KrF excimer laser beam (wavelength: 248 nm), EUV (wavelength: 13.5 mm), or an electron beam is more preferred; and an ArF excimer laser beam, EUV, or an electron beam is still more preferred.

It is preferred that post exposure baking (hereinafter, may be also referred to as "PEB") is carried out after the exposure to promote dissociation of the acid-labile group included in the polymer (A) and the like mediated by the acid generated from the compound (B), etc. upon the exposure in light-exposed regions of the resist film. This PEB enables an increase in a difference in solubility of the resist film in a developer solution between the light-exposed regions and light-unexposed regions. The lower limit of a PEB temperature is preferably 50° C., more preferably 80° C., and still more preferably 100° C. The upper limit of the PEB temperature is preferably 180° C., and more preferably 130° C. The lower limit of a PEB time period is preferably 5 sec, more preferably 10 sec, and still more preferably 30 sec. The upper limit of the PEB time period is preferably 600 sec, more preferably 300 sec, and still more preferably 100 sec.

Developing Step

In this step, the resist film exposed is developed. Accordingly, formation of a predetermined resist pattern is enabled. The development is typically followed by washing with a rinse agent such as water or an alcohol and then drying. The development procedure in the developing step may be carried out by either development with an alkali, or development with an organic solvent.

In the case of the development with an alkali, the developer solution for use in the development is exemplified by: alkaline aqueous solutions prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (hereinafter, may be also referred to as "TMAH"), pyrrole, piperidine, choline, 1,8-diazabicyclo-[5.4.0]-7-undecene, and 1,5-diazabicyclo-[4.3.0]-5-nonene; and the like. Of these, an aqueous TMAH solution is preferred, and a 2.38% by mass aqueous TMAH solution is more preferred.

In the case of the development with an organic solvent, the developer solution is exemplified by: an organic solvent such as a hydrocarbon solvent, an ether solvent, an ester solvent, a ketone solvent, and an alcohol solvent; a solution containing the organic solvent; and the like. An exemplary organic solvent includes one, or two or more types of the solvents exemplified as the organic solvent (D) of the radiation-sensitive resin composition of the one embodiment of the present invention, and the like. Of these, the ester solvent or the ketone solvent is preferred. The ester solvent is preferably an acetic acid ester solvent, and more preferably n-butyl acetate. The ketone solvent is preferably the chain ketone, and more preferably 2-heptanone. The lower limit of a content of the organic solvent in the developer solution is preferably 80% by mass, more preferably 90% by mass, still more preferably 95% by mass, and particularly preferably 99% by mass. Components other than the organic solvent in the developer solution are exemplified by water, silicone oil, and the like.

Examples of the development procedure include: a dipping procedure in which the substrate is immersed for a given time period in the developer solution charged in a container; a puddle procedure in which the developer solution is placed to form a dome-shaped bead by way of the surface tension on the surface of the substrate for a given time period to conduct a development; a spraying procedure in which the developer solution is sprayed onto the surface of the substrate; a dynamic dispensing procedure in which the developer solution is continuously dispensed onto the substrate, which is rotated at a constant speed, while scanning with a developer solution-dispensing nozzle at a constant speed; and the like.

The pattern to be formed according to the method of forming a resist pattern is exemplified by a line-and-space pattern, a hole pattern, and the like.

Compound

The compound of the still another embodiment of the present invention has been described as the compound (B) of the radiation-sensitive resin composition of the one embodiment of the present invention, described above. The compound may be suitably used as a radiation-sensitive acid generating agent in a radiation-sensitive resin composition.

EXAMPLES

Hereinafter, the present invention is explained in detail by way of Examples, but the present invention is not in any way limited to these Examples. Measuring methods for various types of physical property values are shown below.

Weight Average Molecular Weight (Mw), Number Average Molecular Weight (Mn), and Dispersity Index (Mw/Mn)

Measurements of the Mw and the Mn of the polymer were carried out by gel permeation chromatography (GPC) using GPC columns available from Tosoh Corporation ("G2000 HXL"×2, "G3000 HXL"×1, and "G4000 HXL"×1) under the following conditions.

elution solvent: tetrahydrofuran flow rate: 1.0 mL/min sample concentration: 1.0% by mass amount of injected sample: 100 uL column temperature: 40° C.

detector: differential refractometer standard substance: mono-dispersed polystyrene Proportion of Structural Unit The proportion of each structural unit in the polymer was measured by a $^{13}$C-NMR analysis using a nuclear magnetic resonance apparatus ("JNM-Delta400" available from JEOL, Ltd.).

Synthesis of Polymers

Monomers (hereinafter, may be also referred to as "monomers (M-1) to (M-26)") represented by the following formulae (M-1) to (M-26) were used in synthesis of the polymer (A). Furthermore, the monomer (M-1), the monomer (M-2), and monomers (hereinafter, may be also referred to as "monomers (M-27) to (M-28)") represented by the following formulae (M-27) to (M-28) were used for synthesis of the polymer (E). It is to be noted that in the following Synthesis Examples, unless otherwise specified particularly, the term "parts by mass" means a value, provided that the total mass of the monomers used was 100 parts by mass, and the term "mol %" means a value, provided that the total mol number of the monomers used was 100 mol %.

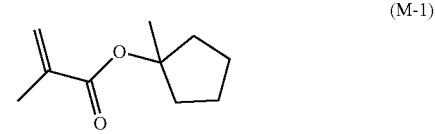

(M-1)

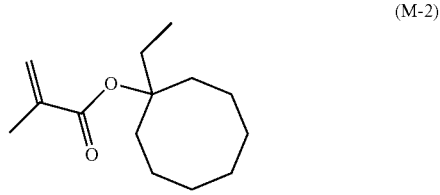

(M-2)

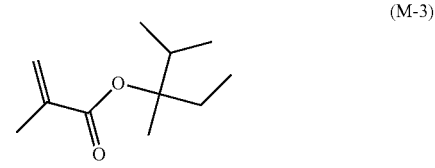

(M-3)

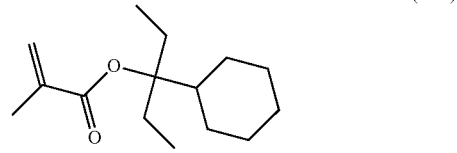

(M-4)

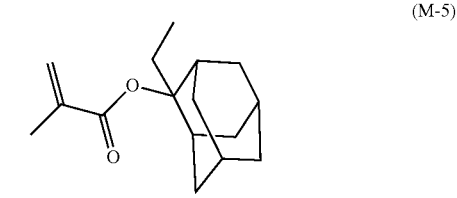

(M-5)

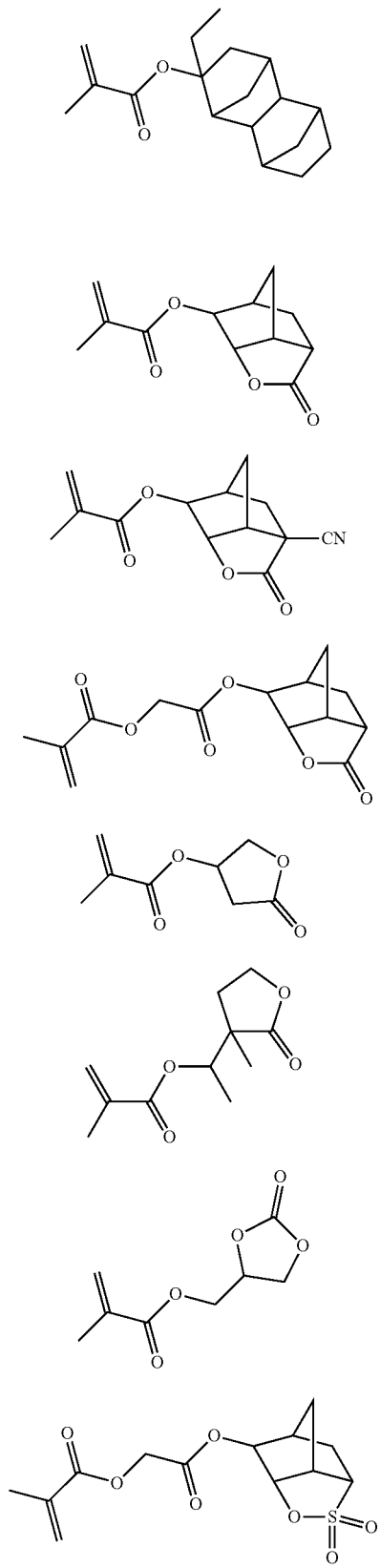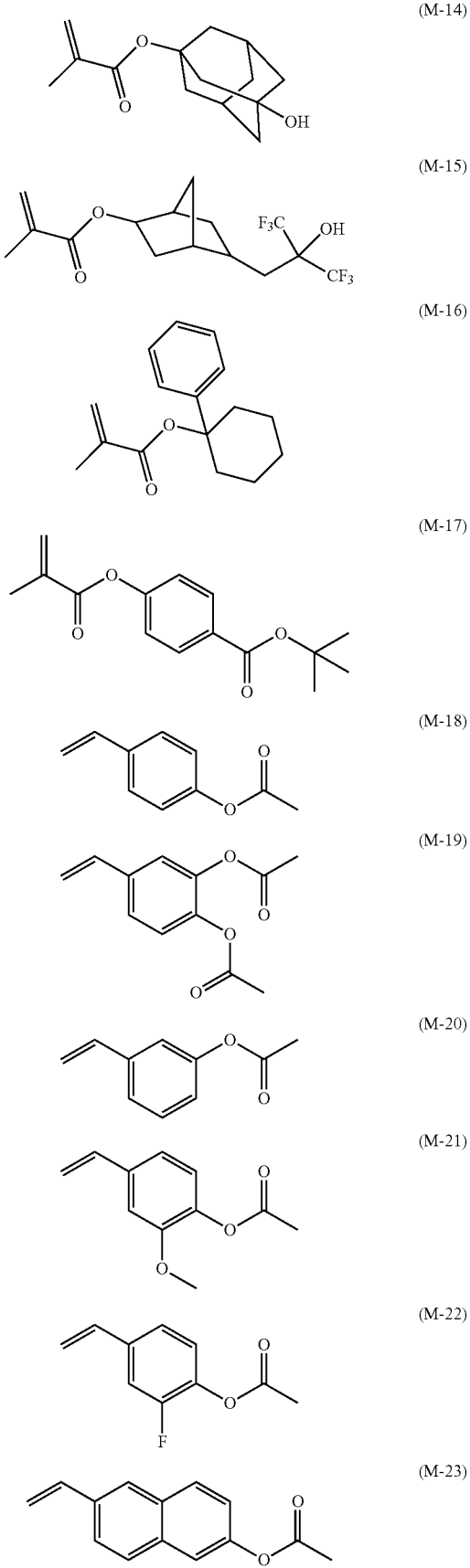

-continued

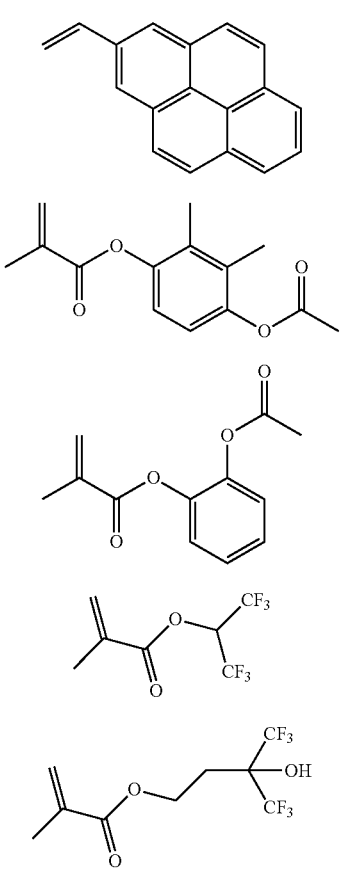

Synthesis of Polymer (A)

Synthesis Example 1: Synthesis of Polymer (A-1)

The monomer (M-1) and the monomer (M-10) were dissolved in 200 parts by mass of 2-butanone such that the molar ratio became 45/55. Next, 5 mol % azobisisobutyronitrile was added as an initiator to prepare a monomer solution. Meanwhile, 100 parts by mass of 2-butanone were charged into a reaction vessel, which was then purged with nitrogen for 30 min. The temperature inside the reaction vessel was elevated to 80° C., and the monomer solution was added dropwise thereto over 3 hrs with stirring. The time of starting the dropwise addition was regarded as the time of starting the polymerization reaction, and the polymerization reaction was allowed to proceed for 6 hrs. After completion of the polymerization reaction, the polymerization solution was cooled to no greater than 30° C. by water cooling. The thus cooled polymerization solution was charged into 2,000 parts by mass of methanol, and a thus precipitated white powder was filtered off. The white powder obtained by the filtration was washed twice with 400 parts by mass of methanol and filtered off, followed by drying at 60° C. for 15 hrs to give a white powdery polymer (A-1) (yield: 67%). The Mw of the polymer (A-1) thus obtained was 6,803, and the Mw/Mn was 1.43. Furthermore, as a result of the $^{13}$C-NMR analysis, proportions of the structural units derived from the monomer (M-1) and the monomer (M-10) in the polymer (A-1) were 42 mol % and 58 mol %, respectively.

Synthesis Examples 2 to 10: Synthesis of Polymers (A-2) to (A-10)

Polymers (A-2) to (A-10) were synthesized by an operation similar to that of Synthesis Example 1 except that monomers of the type and in the proportion shown in Table 1 below were used.

Synthesis Example 11: Synthesis of Polymer (A-11)

The monomer (M-1), the monomer (M-17), and the monomer (M-18) were dissolved in 200 parts by mass of propylene glycol 1-monomethyl ether such that the molar ratio became 30/10/60. Next, 4 mol % azobisisobutyronitrile was added as an initiator to prepare a monomer solution. Meanwhile, 100 parts by mass of propylene glycol 1-monomethyl ether were charged into an empty reaction vessel, and heated to 85° C. with stirring. Next, the monomer solution thus prepared was added dropwise thereto over 3 hrs, followed by heating at 85° C. for 3 hrs, whereby the polymerization reaction was conducted for a total of 6 hrs. After completion of the polymerization reaction, the polymerization solution was cooled to room temperature. The thus cooled polymerization solution was charged into 500 parts by mass of hexane with respect to the polymerization solution, and a thus precipitated white powder was filtered off. The white powder obtained by the filtration was washed twice with 100 parts by mass of hexane with respect to the polymerization solution and filtered off, followed by dissolving in 300 parts by mass of propylene glycol 1-monomethyl ether. Next, 500 parts by mass of methanol, 50 parts by mass of triethylamine, and 10 parts by mass of ultra-pure water were added to a resulting solution, and a hydrolysis reaction was performed at 70° C. for 6 hrs with stirring. After completion of the hydrolysis reaction, the remaining solvent was distilled away and a solid thus obtained was dissolved in 100 parts by mass of acetone. The solution was added dropwise to 500 parts by mass of water to permit coagulation of the resin, and a solid thus obtained was filtered off. Drying at 50° C. for 12 hours gave a white powdery polymer (A-11) (yield: 62%). The Mw of the polymer (A-11) thus obtained was 6,981, and the Mw/Mn was 1.61. Furthermore, as a result of the $^{13}$C-NMR analysis, proportions of the structural units derived from the monomer (M-1), the monomer (M-17), and the monomer (M-18) in the polymer (A-11) were 27 mol %, 9 mol %, and 64 mol %, respectively.

Synthesis Examples 12 to 19: Synthesis of Polymers (A-12) to (A-19)

Polymers (A-12) to (A-19) were synthesized by an operation similar to that of Synthesis Example 11 except that monomers of the type and in the proportion shown in Table 1 below were used.

The amount used of the monomers that give each structural unit, the proportions of the structural units, the yield, the Mw, and the Mw/Mn of each polymer (A) obtained in Synthesis Examples 1 to 19 are shown in Table 1 below. It is to be noted that in the Table 1, "-" indicates that the corresponding monomer was not used.

TABLE 1

| (A) Polymer | Monomer that gives structural unit (I) | | | Monomer that gives structural unit (II) | | |
|---|---|---|---|---|---|---|
| | type | amount used (mol %) | proportion of structural unit (mol %) | type | amount used (mol %) | proportion of structural unit (mol %) |
| Synthesis Example 1 | A-1 | M-1 | 45 | 42 | M-10 | 55 | 58 |
| Synthesis Example 2 | A-2 | M-3 | 45 | 42 | M-10 | 40 | 42 |
| | | | | | M-11 | 15 | 16 |
| Synthesis Example 3 | A-3 | M-1 | 35 | 33 | M-9 | 50 | 54 |
| | | M-2 | 15 | 13 | | | |
| Synthesis Example 4 | A-4 | M-3 | 35 | 32 | M-7 | 45 | 50 |
| | | M-4 | 90 | 18 | | | |
| Synthesis Example 5 | A-5 | M-1 | 35 | 33 | M-12 | 40 | 45 |
| | | M-5 | 25 | 22 | | | |
| Synthesis Example 6 | A-6 | M-1 | 35 | 32 | M-8 | 45 | 50 |
| | | M-6 | 20 | 18 | | | |
| Synthesis Example 7 | A-7 | M-3 | 40 | 38 | M-13 | 45 | 49 |
| | | M-5 | 15 | 13 | | | |
| Synthesis Example 8 | A-8 | M-4 | 55 | 50 | M-10 | 35 | 38 |
| Synthesis Example 9 | A-9 | M-1 | 45 | 42 | M-10 | 40 | 44 |
| Synthesis Example 10 | A-10 | M-3 | 55 | 50 | M-9 | 20 | 23 |
| | | | | | M-10 | 25 | 27 |
| Synthesis Example 11 | A-11 | M-1 | 30 | 27 | — | — | — |
| | | M-17 | 10 | 9 | | | |
| Synthesis Example 12 | A-12 | M-3 | 35 | 32 | — | — | — |
| | | M-16 | 20 | 18 | | | |
| Synthesis Example 13 | A-13 | M-1 | 35 | 32 | — | — | — |
| | | M-6 | 10 | 9 | | | |
| Synthesis Example 14 | A-14 | M-4 | 35 | 33 | — | — | — |
| Synthesis Example 15 | A-15 | M-3 | 50 | 47 | — | — | — |
| Synthesis Example 16 | A-16 | M-1 | 45 | 44 | — | — | — |
| Synthesis Example 17 | A-17 | M-4 | 50 | 47 | — | — | — |
| Synthesis Example 18 | A-18 | M-1 | 45 | 43 | — | — | — |
| Synthesis Example 19 | A-19 | M-3 | 40 | 38 | — | — | — |

| | Monomer that gives structural unit (III) | | Monomer that gives other structural unit | | | | |
|---|---|---|---|---|---|---|---|
| | type | amount used (mol %) | proportion of structural unit (mol %) | type | amount used (mol %) | propoition of structural unit (mol %) | Yield (%) | Mw | Mw/Mn |
| Synthesis Example 1 | — | — | — | — | — | — | 67 | 6,803 | 1.43 |
| Synthesis Example 2 | — | — | — | — | — | — | 71 | 7,001 | 1.55 |
| Synthesis Example 3 | — | — | — | — | — | — | 78 | 7,861 | 1.43 |
| Synthesis Example 4 | — | — | — | — | — | — | 69 | 7,021 | 1.51 |
| Synthesis Example 5 | — | — | — | — | — | — | 65 | 7,144 | 1.42 |
| Synthesis Example 6 | — | — | — | — | — | — | 66 | 6,988 | 1.44 |
| Synthesis Example 7 | — | — | — | — | — | — | 64 | 6,878 | 1.47 |
| Synthesis Example 8 | — | — | — | M-15 | 10 | 12 | 78 | 7,382 | 1.41 |
| Synthesis Example 9 | — | — | — | M-14 | 15 | 14 | 72 | 7,612 | 1.55 |
| Synthesis Example 10 | — | — | — | — | — | — | 74 | 7,221 | 1.56 |
| Synthesis Example 11 | M-18 | 60 | 64 | — | — | — | 62 | 6,981 | 1.61 |
| Synthesis Example 12 | M-19 | 45 | 50 | — | — | — | 61 | 6,817 | 1.55 |

TABLE 1-continued

| | | | | | | | | | |
|---|---|---|---|---|---|---|---|---|---|
| Synthesis Example 13 | M-20 | 55 | 59 | — | — | — | 59 | 6,221 | 1.53 |
| Synthesis Example 14 | M-21 | 55 | 57 | M-15 | 10 | 10 | 69 | 6,002 | 1.58 |
| Synthesis Example 15 | M-18 M-22 | 40 10 | 41 12 | — | — | — | 65 | 6,823 | 1.48 |
| Synthesis Example 16 | M-18 M-23 | 40 15 | 41 15 | — | — | — | 63 | 6,312 | 1.47 |
| Synthesis Example 17 | M-19 | 40 | 42 | M-24 | 10 | 11 | 65 | 6,522 | 1.44 |
| Synthesis Example 18 | M-19 M-25 | 35 20 | 36 21 | — | — | — | 66 | 6,221 | 1.42 |
| Synthesis Example 19 | M-18 M-26 | 40 20 | 41 21 | — | — | — | 61 | 6,421 | 1.49 |

Synthesis of Polymer (E)

Synthesis Example 20: Synthesis of Polymer (E-1)

The monomer (M-1) and the monomer (M-28) were dissolved in 200 parts by mass of 2-butanone such that the molar ratio became 50/50. Next, 5 mol % azobisisobutyronitrile was added as an initiator to prepare a monomer solution. Meanwhile, 100 parts by mass of 2-butanone were charged into a reaction vessel, which was then purged with nitrogen for 30 min. The temperature inside the reaction vessel was elevated to 80° C., and the monomer solution was added dropwise thereto over 3 hrs with stirring. The time of starting the dropwise addition was regarded as the time of starting the polymerization reaction, and the polymerization reaction was allowed to proceed for 6 hrs. After completion of the polymerization reaction, the polymerization solution was cooled to no greater than 30° C. by water cooling. The solvent was replaced with 400 parts by mass of acetonitrile, and then an operation of adding 100 parts by mass of hexane and stirring to collect an acetonitrile layer was repeated three times. The solvent was replaced with propylene glycol monomethyl ether acetate to give a solution of the polymer (E-1) (yield: 79%). The Mw of the polymer (E-1) thus obtained was 4,988, and the Mw/Mn was 1.71. Furthermore, as a result of the $^{13}$C-NMR analysis, proportions of the structural units derived from the monomer (M-1) and the monomer (M-28) in the polymer (E-1) were 47 mol % and 53 mol %, respectively.

Synthesis Example 21: Synthesis of Polymer (E-2)

A polymer (E-2) was synthesized by an operation similar to that of Synthesis Example 20 except that monomers of the type and in the proportion shown in Table 2 below were used.

The amount used of the monomers that give each structural unit, the proportions of the structural units, the yield, the Mw, and the Mw/Mn of each polymer (A) obtained in Synthesis Examples 20 to 21 are shown in Table 2 below.

TABLE 2

| | | Monomer that gives structural unit (I') | | | Monomer that gives other structural unit | | | | |
|---|---|---|---|---|---|---|---|---|---|
| (E) Polymer | type | amount used (mol %) | proportion a structural unit (mol %) | type | amount used (mol %) | proportion of structural unit (mol %) | Yield (%) | Mw | Mw/Mn |
| Synthesis Example 20 | E-1 | M-28 | 50 | 53 | M-1 | 50 | 47 | 79 | 4,988 | 1.71 |
| Synthesis Example 21 | E-2 | M-27 M-28 | 45 20 | 42 25 | M-2 | 35 | 33 | 81 | 5,051 | 1.65 |

Synthesis of Compound (B)

Synthesis Example 22: Synthesis of Compound (B-1)

59.0 mmol of bromoacetylbromide was dissolved in dichloromethane to give a 1 M solution. The solution was cooled to 0° C., a mixed solution of 118.0 mmol of tert-butyl alcohol and 118.0 mmol of pyridine was added thereto at a rate such that a temperature thereof did not exceed 10° C., and then a reaction was allowed to proceed for 1 hour at room temperature. After quenching with an aqueous saturated ammonium chloride solution, an organic layer obtained by extraction with dichloromethane was dried over sodium sulfate. After distilling away the solvent, purification by column chromatography was performed to give tert-butyl-2-bromoacetate (yield: 75%). A synthesis scheme of the tert-butyl-2-bromoacetate is shown below.

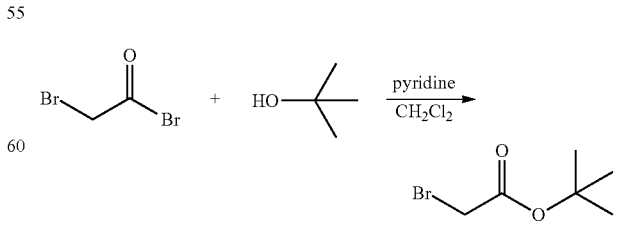

In a reaction vessel, 40.0 mmol of tert-butyl-2-bromoacetate synthesized as described above was dissolved in acetone to give a 1 M solution, and the solution was cooled to 0° C. After 45.0 mmol of sodium thioacetate was charged thereinto gradually over 1 hour, the solution was stirred at room temperature for 1 hour. After completion of the reaction, quenching was performed with an aqueous saturated ammonium chloride solution, dichloromethane was added for extraction, and an organic layer was separated. The organic layer was dried over sodium sulfate and the solvent was distilled away to give tert-butyl-2-(acetylthio)acetate (yield: 95%). A synthesis scheme of the tert-butyl-2-(acetylthio)acetate is shown below.

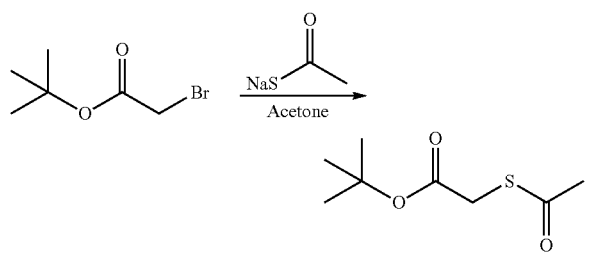

In a reaction vessel, 30.0 mmol of tert-butyl-2-(acetylthio)acetate synthesized as described above was dissolved in a mixed solvent of methanol and water to give a 1 M solution, and the solution was cooled to 0° C. After 33 mL of a 1 M aqueous lithium hydroxide solution was charged thereinto gradually over 1 hour, the solution was stirred at room temperature for 1 hour. After completion of the reaction, toluene was added for extraction, and an organic layer was discarded. An aqueous layer was neutralized with 1 M hydrochloric acid to reach a pH of 5, and then extraction was performed with ethyl acetate to separate the organic layer. The organic layer was dried over sodium sulfate, the solvent was distilled away, and column purification was performed to give tert-butyl-2-mercaptacetate (yield: 91%). A synthesis scheme of the tert-butyl-2-mercaptacetate is shown below.

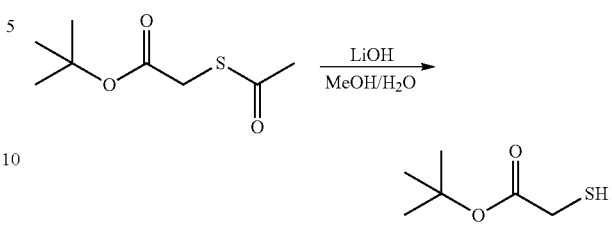

In a reaction vessel, 20 mmol of tert-butyl-2-mercaptacetate and 20 mmol of a compound represented by the following formulae (PB-1) were dissolved in a dimethylformamide solvent so as to be 1 M, and the solution was cooled to 0° C. After the cooling, 22 mmol of potassium carbonate was charged thereinto gradually over 1 hour, and then the solution was stirred at room temperature for 1 hour. After completion of the reaction, quenching was performed with an aqueous saturated ammonium chloride solution, dichloromethane was added for extraction, and an organic layer was separated. The organic layer was dried over sodium sulfate and the solvent was distilled away to give a compound (hereinafter, may be also referred to as "compound (PB-2)") represented by the following formula (PB-2) (yield: 95%). A synthesis scheme of the compound (PB-2) is shown below.

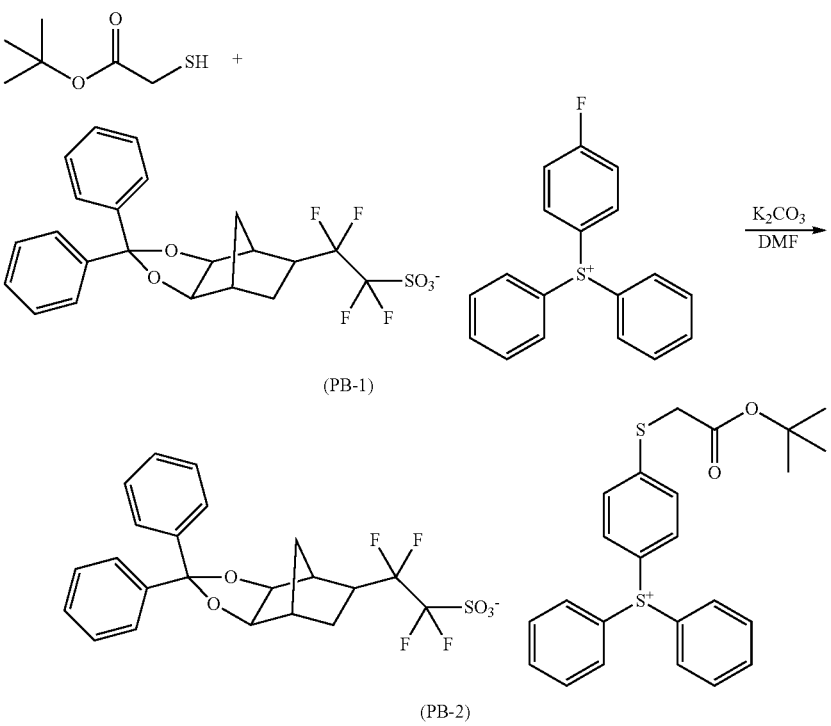

In a reaction vessel, 15 mmol of the compound (PB-2) synthesized as described above was dissolved in a mixed solvent of acetonitrile/water (volume ratio of 3:1) so as to be 1 M, 45 mmol of Oxone (registered trademark) (available from Tokyo Chemical Industry Co., Ltd.) was charged thereinto gradually over 1 hour, and then the solution was stirred at room temperature for 8 hrs. After completion of the reaction, quenching was performed with an aqueous saturated sodium sulfite solution, dichloromethane was added for extraction, and an organic layer was separated. The organic layer was dried over sodium sulfate and the solvent was distilled away, and column purification was performed to give a compound (hereinafter, may be also referred to as "compound (B-1)") represented by the following formula (B-1) (yield: 95%). A synthesis scheme of the compound (B-1) is shown below.

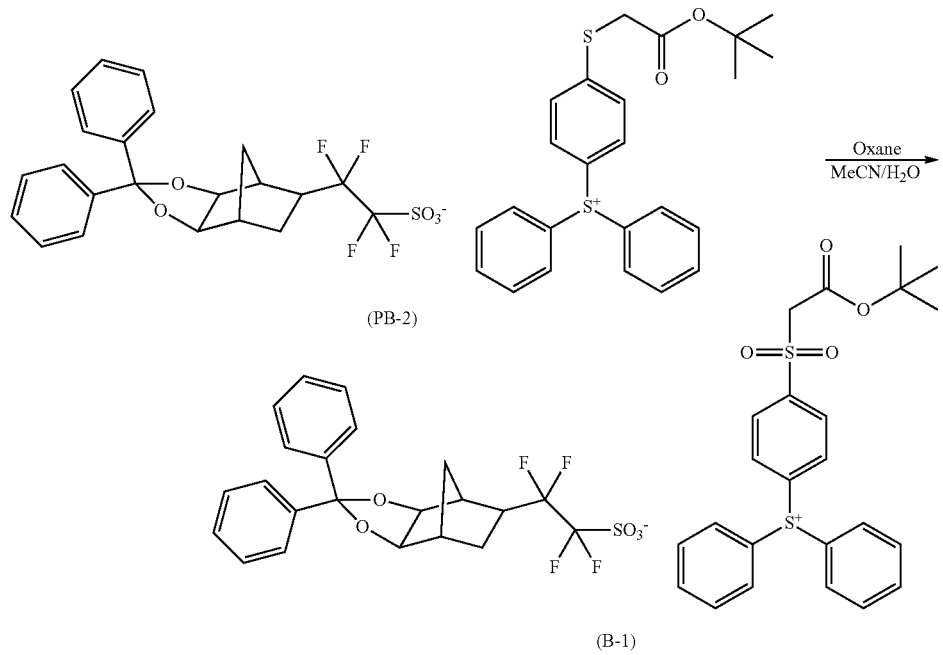

Synthesis Examples 23 to 36: Synthesis of Compounds (B-2) to (B-15)

Compounds (hereinafter, may be also referred to as "compounds (B-2) to (B-15)") represented by the following formulae (B-2) to (B-15) were synthesized by a similar operation to that of Synthesis Example 22, except that a precursor was appropriately changed.

-continued

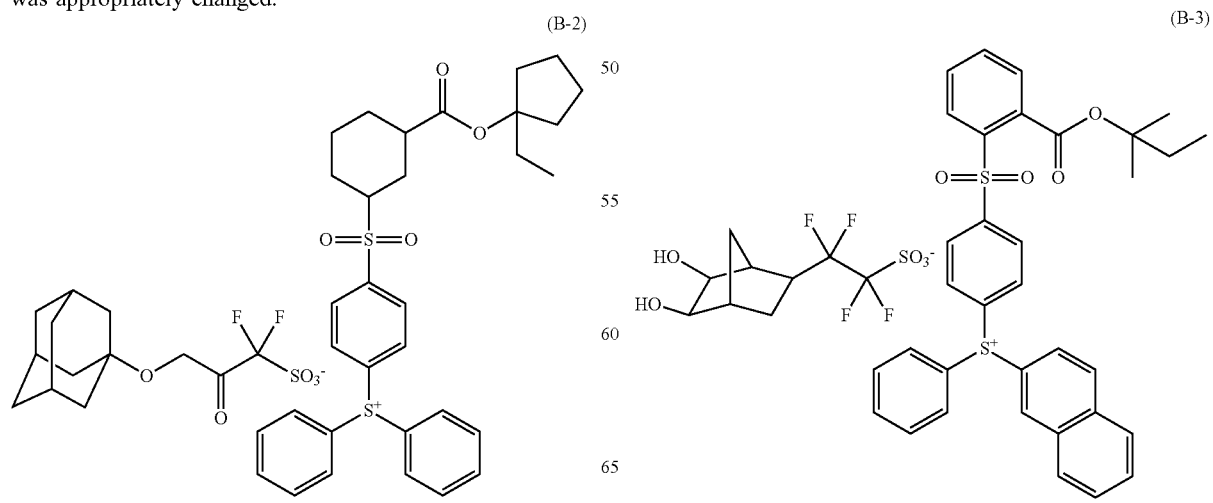

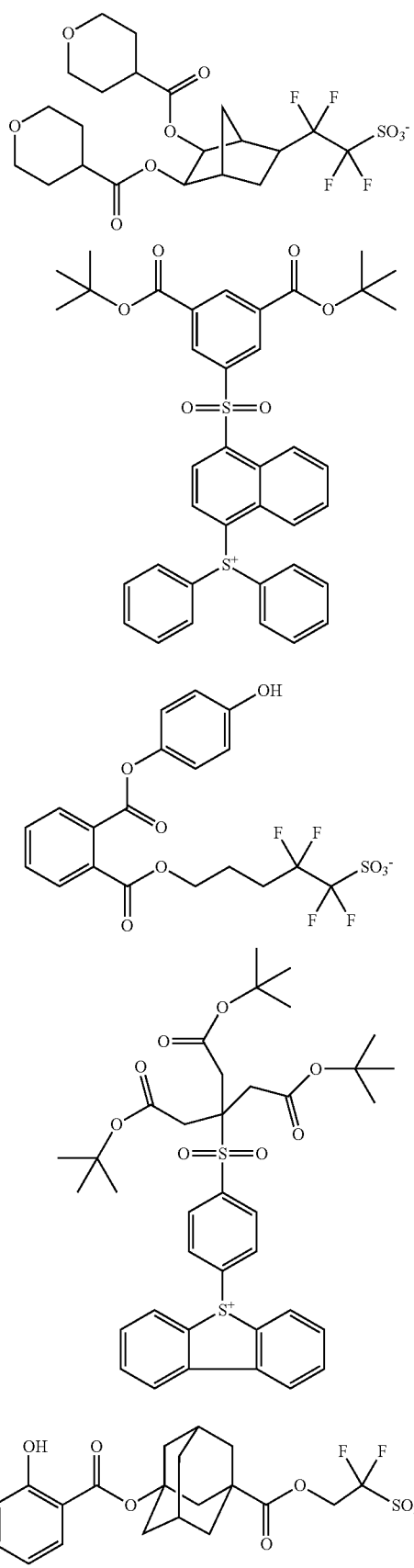
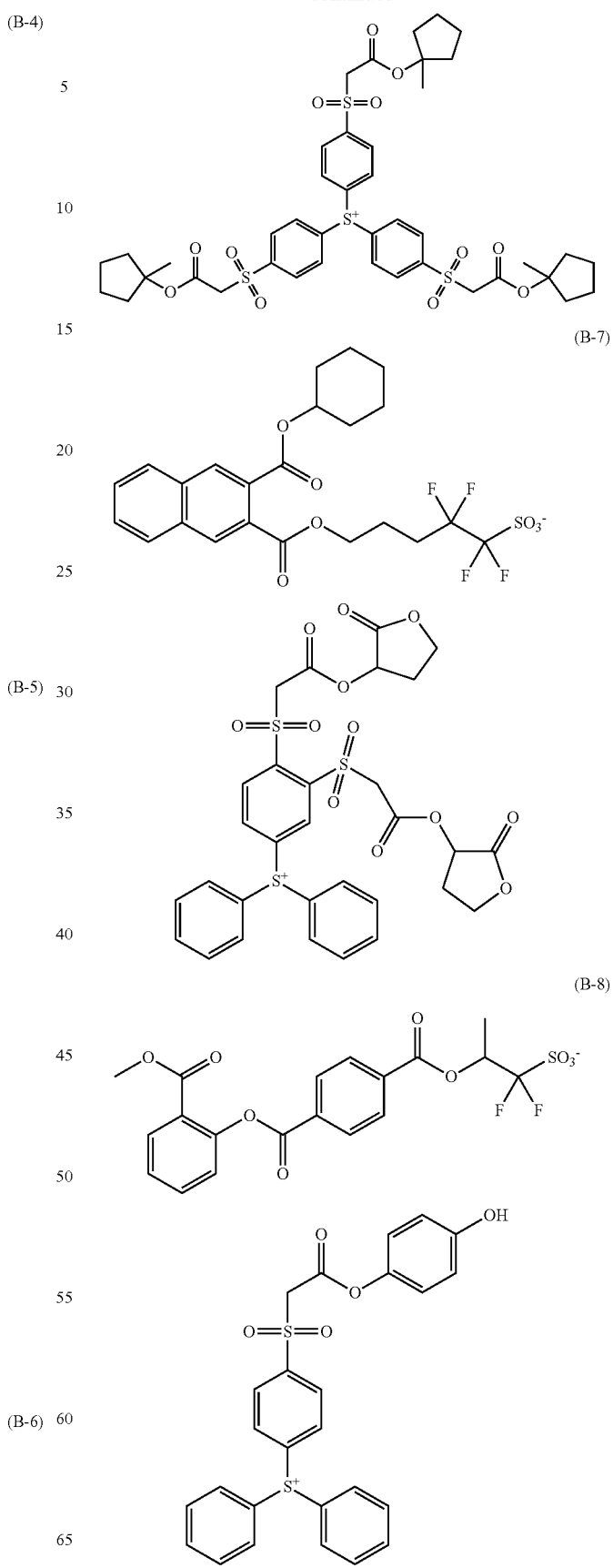

(B-9)
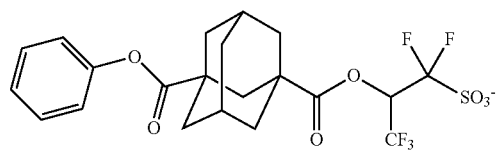
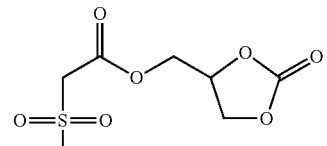
(B-10)
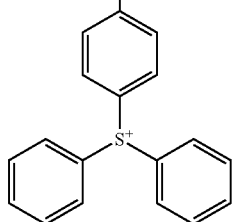
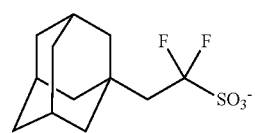
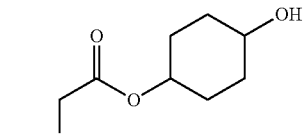
(B-11)
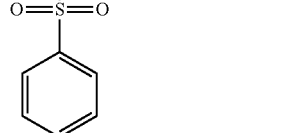
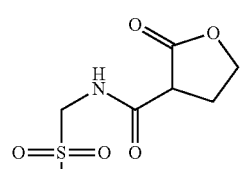
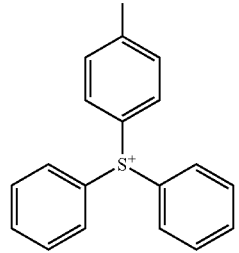
(B-12)
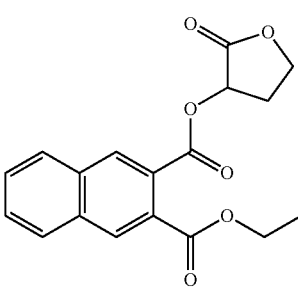
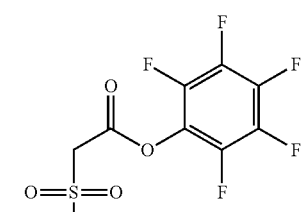
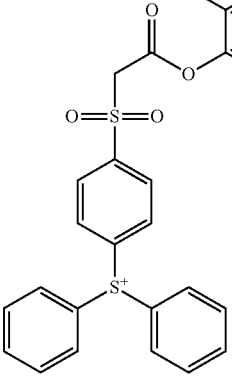
(B-13)
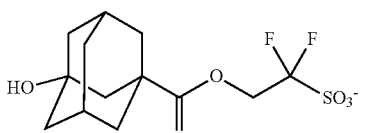
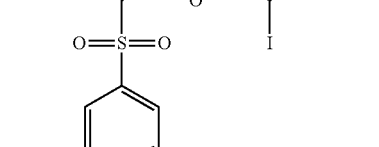
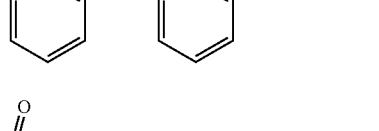
(B-14)
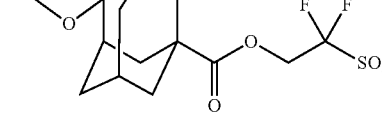

-continued

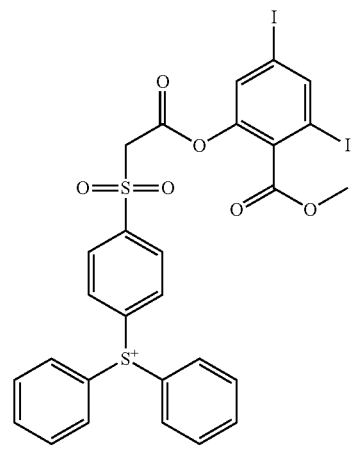

(B-15)

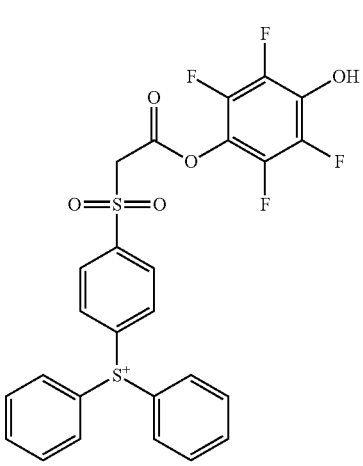

Acid Generating Agent Other than Compound (B)

(B-16) to (B-18): Compounds represented by the following formulae (B-16) to (B-18)

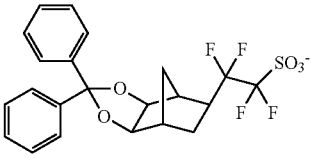

(B-16)

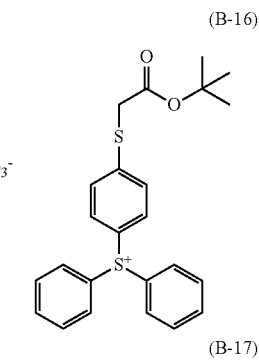

(B-17)

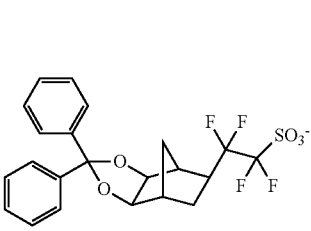

(B-18)

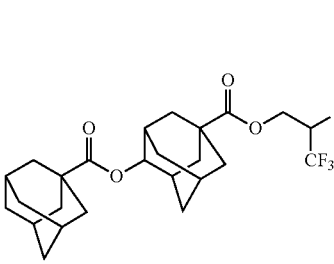

(C) Acid Diffusion Control Agent (C-1) to (C-6): Compounds represented by the following formulae (C-1) to (C-6)

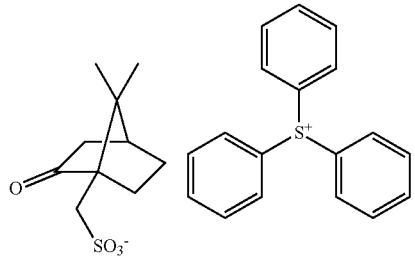

(C-1)

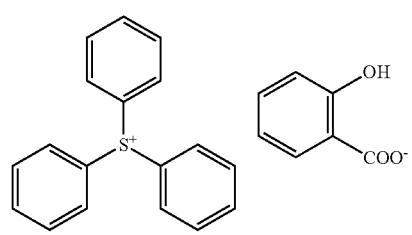

(C-2)

Preparation of Radiation-Sensitive Resin Composition

The acid generating agent other than the compound (B), the acid diffusion control agent (C), and the organic solvent (D) used in preparing each radiation-sensitive resin composition are shown below. It is to be noted that unless otherwise specified particularly, the term "parts by mass" means a value, provided that the mass of the polymer (A) used was 100 parts by mass, and the term "mol %" means a value, provided that the mol number of the compound (B) used was 100 mol %.

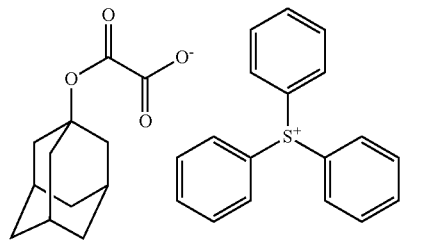

(C-3)

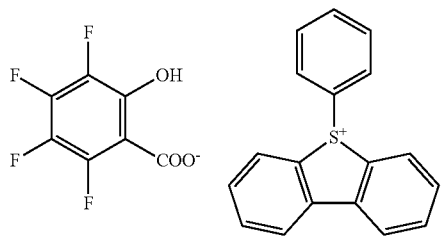

(C-4)

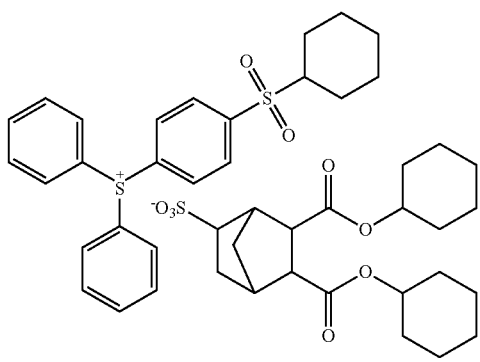

(C-5)

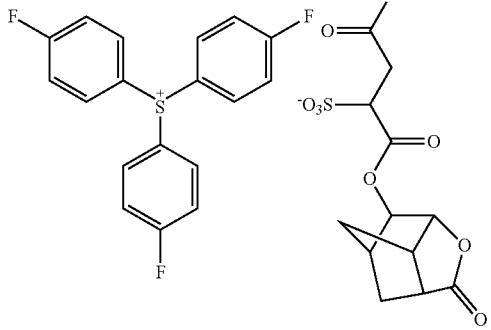

(C-6)

(D) Organic Solvent
D-1: propylene glycol 1-monomethyl ether acetate
D-2: propylene glycol 1-monomethyl ether Preparation of Radiation-Sensitive Resin Composition for ArF Exposure Example 1: Preparation of Radiation-Sensitive Resin Composition (J-1)

A radiation-sensitive resin composition (J-1) was prepared by: mixing 100 parts by mass of (A-1) as the polymer (A), 15 parts by mass of (B-1) as the compound (B), 8.0 parts by mass of (C-1) as the acid diffusion control agent (C), 2,240 parts by mass of (D-1) and 960 parts by mass of (D-2) as the organic solvent (D), and 7 parts by mass of (E-1) as the polymer (E); and filtering a resulting mixture through a membrane filter having a pore size of 0.2 μm.

Examples 2 to 21 and Comparative Examples 1 to 2: Preparation of Radiation-Sensitive Resin Compositions (J-2) to (J-21) and (CJ-1) to (CJ-2)

Radiation-sensitive resin compositions (J-2) to (J-21) and (CJ-1) to (CJ-2) were prepared in a similar manner to Example 1, except that for each component, the type and content shown in Table 3 below were used.

TABLE 3

|  | Radiation-sensitive resin composition | (A) Polymer | | (B) Compound | | (C) Acid diffusion control agent | | (E) Polymer | | (D) Organic solvent | |
|---|---|---|---|---|---|---|---|---|---|---|---|
|  |  | type | content (parts by mass) | type | content (parts by mass) | type | content (parts by mass) | type | content (parts by mass) | type | content (parts by mass) |
| Example 1 | J-1 | A-1 | 100 | B-1 | 15 | C-1 | 8.0 | E-1 | 7 | D-1/D-2 | 2,240/960 |
| Example 2 | J-2 | A-1 | 100 | B-2 | 90 | C-2 | 6.0 | E-1 | 7 | D-1/D-2 | 2,240/960 |
| Example 3 | J-3 | A-1 | 100 | B-3 | 20 | C-5 | 6.0 | E-1 | 7 | D-1/D-2 | 2,240/960 |
| Example 4 | J-4 | A-1 | 100 | B-4 | 15 | C-3 | 5.5 | E-1 | 7 | D-1/D-2 | 2,240/960 |
| Example 5 | J-5 | A-1 | 100 | B-5 | 15 | C-4 | 8.5 | E-1 | 7 | D-1/D-2 | 2,240/960 |
| Example 6 | J-6 | A-1 | 100 | B-6 | 25 | C-4 | 8.5 | E-1 | 7 | D-1/D-2 | 2,240/960 |
| Example 7 | J-7 | A-1 | 100 | B-7 | 20 | C-5 | 6.0 | E-1 | 7 | D-1/D-2 | 2,240/960 |
| Example 8 | J-8 | A-1 | 100 | B-8 | 20 | C-6 | 7.5 | E-1 | 7 | D-1/D-2 | 2,240/960 |
| Example 9 | J-9 | A-1 | 100 | B-9 | 15 | C-2 | 5.0 | E-1 | 7 | D-1/D-2 | 2,240/960 |
| Example 10 | J-10 | A-1 | 100 | B-10 | 10 | C-2 | 8.0 | E-1 | 7 | D-1/D-2 | 2,240/960 |
| Example 11 | J-11 | A-1 | 100 | B-11 | 20 | C-2 | 6.0 | E-1 | 7 | D-1/D-2 | 2,240/960 |
| Example 12 | J-12 | A-2 | 100 | B-1 | 20 | C-2 | 6.0 | E-1 | 7 | D-1/D-2 | 2,240/960 |
| Example 13 | J-13 | A-3 | 100 | B-2 | 15 | C-3 | 7.0 | E-1 | 7 | D-1/D-2 | 2,240/960 |

TABLE 3-continued

| Radiation-sensitive resin composition | (A) Polymer type | content (parts by mass) | (B) Compound type | content (parts by mass) | (C) Acid diffusion control agent type | content (parts by mass) | (E) Polymer type | content (parts by mass) | (D) Organic solvent type | content (parts by mass) |
|---|---|---|---|---|---|---|---|---|---|---|
| Example 14 | J-14 | A-4 | 100 | B-4 | 20 | C-1 | 8.0 | E-1 | 7 | D-1/D-2 | 2,240/960 |
| Example 15 | J-15 | A-5 | 100 | B-1 | 20 | C-1 | 8.5 | E-1 | 7 | D-1/D-2 | 2,240/960 |
| Example 16 | J-16 | A-6 | 100 | B-3 | 15 | C-2 | 5.5 | E-1 | 7 | D-1/D-2 | 2,240/960 |
| Example 17 | J-17 | A-7 | 100 | B-1 | 15 | C-4 | 7.5 | E-1 | 7 | D-1/D-2 | 2,240/960 |
| Example 18 | J-18 | A-8 | 100 | B-2 | 10 | C-2 | 5.5 | E-1 | 7 | D-1/D-2 | 2,240/960 |
| Example 19 | J-19 | A-9 | 100 | B-1 | 15 | C-1 | 7.5 | E-1 | 7 | D-1/D-2 | 2,240/960 |
| Example 20 | J-20 | A-10 | 100 | B-1 | 15 | C-4 | 8.0 | E-1 | 7 | D-1/D-2 | 2,240/960 |
| Example 21 | J-21 | A-1 | 100 | B-1 | 10 | C-1 | 7.5 | E-1 | 7 | D-1/D-2 | 2,240/960 |
|  |  |  |  | B-18 | 5 |  |  |  |  |  |  |
| Comparative Example 1 | CJ-1 | A-1 | 100 | B-16 | 15 | C-1 | 8.0 | E-1 | 7 | D-1/D-2 | 2,240/960 |
| Comparative Example 2 | CJ-2. | A-1 | 100 | B-17 | 15 | C-1 | 8.0 | E-1 | 7 | D-1/D-2 | 2,240/960 |

Formation of Resist Pattern Using Radiation-Sensitive Resin Composition for ArF Exposure An underlayer antireflective film having an average thickness of 105 nm was formed by applying a composition for underlayer antireflective film formation ("ARC66," available from Brewer Science, Inc.) on a 12-inch silicon wafer using a spin-coater ("CLEAN TRACK ACT 12," available from Tokyo Electron Limited), and thereafter heating the composition at 205° C. for 60 sec. Each radiation-sensitive resin composition for ArF exposure prepared as described above was applied on the underlayer antireflective film using the spin-coater, and subjected to PB at 120° C. for 50 sec. Thereafter, by cooling at 23° C. for 30 sec, a resist film having an average thickness of 90 nm was formed. Next, the resist film was exposed using an ArF excimer laser immersion scanner ("TWINSCAN XT-1900i," available from ASML Co.) through a mask pattern for resist pattern formation, having spaces of 44 nm and a pitch of 102 nm under optical conditions involving: NA of 1.35, and Annular (σ=0.8/0.6). After the exposure, PEB (post-exposure baking) was carried out at 90° C. for 60 sec. Thereafter, the resist film was subjected to puddle development at 23° C. for 10 sec using a 2.38% by mass aqueous TMAH solution, and spin-dried by spinning at 2,000 rpm for 15 sec to form a resist pattern having 45 nm spaces.

Evaluations

The resist patterns formed using the radiation-sensitive resin compositions for ArF exposure were evaluated on the sensitivity, the CDU performance, and the LWR performance in accordance with the following methods. The results are shown in Table 4 below. It is to be noted that line width measurement of the resist patterns was performed using a scanning electron microscope ("CG-5000," available from Hitachi High-Technologies Corporation).

Sensitivity

An exposure dose at which a 40 nm line-and-space pattern was formed in the aforementioned resist pattern formation using the radiation-sensitive resin composition for ArF exposure was defined as an optimum exposure dose, and this optimum exposure dose was adopted as Eop (unit: mJ/cm$^2$). The sensitivity was evaluated to be: "favorable" in a case of the Eop being no greater than 25 mJ/cm$^2$; and "unfavorable" in a case of the Eop being greater than 25 mJ/cm$^2$.

CDU Performance

A mask size was adjusted such that a pattern with 45 nm hole diameters and 110 nm pitch was formed by irradiating at the exposure dose of Eop determined as in the evaluation of "Sensitivity" above, and a resist pattern was formed. The resist pattern thus formed was observed from above using the scanning electron microscope. An averaged value of hole diameters at 16 sites measured in a region of 500 nm was determined, the average value of the hole diameters was measured at 500 sites in total at arbitrary locations, and then a 1 Sigma value was determined from distribution of the measurement values and defined as "CDU" (unit: nm). The CDU value being smaller indicates more favorable CDU performance, revealing less variance of the hole diameters in greater ranges. The CDU performance was evaluated to be: "favorable" in a case of CDU being no greater than 6.0 nm; and "unfavorable" in a case of CDU being greater than 6.0 nm.

LWR Performance

A mask size was adjusted such that a pattern with 45 nm spaces and 800 nm pitch was formed by irradiating at the exposure dose of Eop determined as in the evaluation of "Sensitivity" above, and a resist pattern was formed. The resist pattern thus formed was observed from above using the scanning electron microscope. A total of 500 line widths were measured at arbitrary sites, and then a 3 Sigma value was determined from distribution of the measurement values and the 3 Sigma value was defined as LWR (unit: nm). The LWR value being smaller indicates more favorable LWR performance, revealing less unevenness of the lines. The LWR performance was evaluated to be: "favorable" in a case of the LWR being no greater than 5.8 nm; and "unfavorable" in a case of the LWR being greater than 5.8 nm.

TABLE 4

| Radiation-sensitive resin composition | Eop (mJ/cm$^2$) | CDU (nm) | LWR (nm) |
|---|---|---|---|
| Example 1 | J-1 | 24 | 5.52 | 5.24 |
| Example 2 | J-2 | 23 | 5.22 | 5.01 |
| Example 3 | J-3 | 23 | 5.41 | 5.09 |
| Example 4 | J-4 | 25 | 5.25 | 4.73 |
| Example 5 | J-5 | 24 | 5.11 | 4.83 |
| Example 6 | J-6 | 24 | 5.42 | 5.20 |
| Example 7 | J-7 | 21 | 5.89 | 5.71 |
| Example 8 | J-8 | 23 | 5.88 | 5.53 |
| Example 9 | J-9 | 22 | 5.82 | 5.59 |
| Example 10 | J-10 | 23 | 5.90 | 5.61 |
| Example 11 | J-11 | 24 | 5.92 | 5.68 |
| Example 12 | J-12 | 24 | 5.52 | 5.27 |

TABLE 4-continued

| | Radiation-sensitive resin composition | Eop (mJ/cm$^2$) | CDU (nm) | LWR (nm) |
|---|---|---|---|---|
| Example 13 | J-13 | 23 | 5.32 | 5.03 |
| Example 14 | J-14 | 25 | 5.37 | 5.04 |
| Example 15 | J-15 | 22 | 5.28 | 5.00 |
| Example 16 | J-16 | 24 | 5.22 | 5.01 |
| Example 17 | J-17 | 25 | 5.48 | 5.23 |
| Example 18 | J-18 | 24 | 5.44 | 5.21 |
| Example 19 | J-19 | 23 | 5.55 | 5.28 |
| Example 20 | J-20 | 25 | 5.41 | 5.17 |
| Example 21 | J-21 | 25 | 5.59 | 5.36 |
| Comparative Example 1 | CJ-1 | 34 | 6.49 | 6.17 |
| Comparative Example 2 | CJ-2 | 33 | 6.44 | 6.12 |

As is clear from the results shown in Table 4, all the radiation-sensitive resin compositions for ArF exposure of the Examples were favorable in terms of the sensitivity, the CDU performance, and the LWR performance, as compared with the radiation-sensitive resin compositions of the Comparative Examples.

Preparation of Radiation-Sensitive Resin Composition for EUV Exposure

Example 22: Preparation of Radiation-Sensitive Resin Composition (J-22)

A radiation-sensitive resin composition (J-22) was prepared by: mixing 100 parts by mass of (A-11) as the polymer (A), 35 parts by mass of (B-1) as the compound (B), 10.5 parts by mass of (C-2) as the acid diffusion control agent (C), 4,280 parts by mass of (D-1) and 1,830 parts by mass of (D-2) as the organic solvent (D), and 7 parts by mass of (E-1) as the polymer (E); and filtering a resulting mixture through a membrane filter having a pore size of 0.2 μm.

Examples 23 to 45 and Comparative Examples 3 to 4: Preparation of Radiation-Sensitive Resin Compositions (J-23) to (J-45) and (CJ-3) to (CJ-4)

Radiation-sensitive resin compositions (J-23) to (J-45) and (CJ-3) to (CJ-4) were prepared in a similar manner to Example 22, except that for each component, the type and content shown in Table 5 below were used.

TABLE 5

| | Radiation-sensitive resin composition | (A) Polymer type | content (parts by mass) | (B) Compound type | content (parts by mass) | (C) Acid diffusion control agent type | content (parts by mass) | (E) Polymer type | content (parts by mass) | (D) Organic solvent type | content (parts by mass) |
|---|---|---|---|---|---|---|---|---|---|---|---|
| Example 22 | J-22 | A-11 | 100 | B-1 | 35 | C-2 | 10.5 | E-2 | 7 | D-1/D-2 | 4,280/1,830 |
| Example 23 | J-23 | A-11 | 100 | B-2 | 40 | C-2 | 12.0 | E-2 | 7 | D-1/D-2 | 4,280/1,830 |
| Example 24 | J-24 | A-11 | 100 | B-3 | 30 | C-2 | 11.0 | E-2 | 7 | D-1/D-2 | 4,280/1,830 |
| Example 25 | J-25 | A-11 | 100 | B-4 | 45 | C-3 | 9.5 | E-2 | 7 | D-1/D-2 | 4,280/1,830 |
| Example 26 | J-26 | A-11 | 100 | B-5 | 50 | C-2 | 10.5 | E-2 | 7 | D-1/D-2 | 4,280/1,830 |
| Example 27 | J-27 | A-11 | 100 | B-6 | 45 | C-2 | 11.0 | E-2 | 7 | D-1/D-2 | 4,280/1,830 |
| Example 28 | J-28 | A-11 | 100 | B-7 | 25 | C-3 | 8.0 | E-2 | 7 | D-1/D-2 | 4,280/1,830 |
| Example 29 | J-29 | A-11 | 100 | B-8 | 30 | C-2 | 8.5 | E-2 | 7 | D-1/D-2 | 4,280/1,830 |
| Example 30 | J-30 | A-11 | 100 | B-9 | 35 | C-3 | 10.5 | E-2 | 7 | D-1/D-2 | 4,280/1,830 |
| Example 31 | J-31 | A-11 | 100 | B-10 | 40 | C-3 | 18.5 | E-2 | 7 | D-1/D-2 | 4,280/1,830 |
| Example 32 | J-32 | A-11 | 100 | B-11 | 35 | C-2 | 20.0 | E-2 | 7 | D-1/D-2 | 4,280/1,830 |
| Example 33 | J-33 | A-11 | 100 | B-12 | 30 | C-3 | 10.5 | E-2 | 7 | D-1/D-2 | 4,280/1,830 |
| Example 34 | J-34 | A-11 | 100 | B-13 | 40 | C-2 | 15.0 | E-2 | 7 | D-1/D-2 | 4,280/1,830 |
| Example 35 | J-35 | A-11 | 100 | B-14 | 30 | C-3 | 10.5 | E-2 | 7 | D-1/D-2 | 4,280/1,830 |
| Example 36 | J-36 | A-11 | 100 | B-15 | 45 | C-2 | 16.5 | E-2 | 7 | D-1/D-2 | 4,280/1,830 |
| Example 37 | J-37 | A-12 | 100 | B-1 | 40 | C-2 | 9.5 | E-2 | 7 | D-1/D-2 | 4,280/1,830 |
| Example 38 | J-38 | A-13 | 100 | B-2 | 35 | C-2 | 10.5 | E-2 | 7 | D-1/D-2 | 4,280/1,830 |
| Example 39 | J-39 | A-14 | 100 | B-4 | 30 | C-2 | 12.0 | E-2 | 7 | D-1/D-2 | 4,280/1,830 |
| Example 40 | J-40 | A-15 | 100 | B-1 | 40 | C-2 | 11.5 | E-2 | 7 | D-1/D-2 | 4,280/1,830 |
| Example 41 | J-41 | A-16 | 100 | B-3 | 35 | C-2. | 10.0 | E-2 | 7 | D-1/D-2 | 4,280/1,830 |
| Example 42 | J-42 | A-17 | 100 | B-1 | 40 | C-2 | 9.5 | E-2 | 7 | D-1/D-2 | 4,280/1,830 |
| Example 43 | J-43 | A-18 | 100 | B-2 | 45 | C-2 | 10.5 | E-2 | 7 | D-1/D-2 | 4,280/1,830 |
| Example 44 | J-44 | A-19 | 100 | B-1 | 30 | C-2 | 11.5 | E-2 | 7 | D-1/D-2 | 4,280/1,830 |
| Example 45 | J-45 | A-11 | 100 | B-1 B-18 | 30 15 | C-2 | 8.5 | E-2 | 7 | D-1/D-2 | 4,280/1,830 |
| Comparative Example 3 | CJ-3 | A-11 | 100 | B-16 | 35 | C-2. | 10.5 | E-2 | 7 | D-1/D-2 | 4,280/1,830 |
| Comparative Example 4 | CJ-4 | A-11 | 100 | B-17 | 35 | C-2. | 10.5 | E-2 | 7 | D-1/D-2 | 4,280/1,830 |

Formation of Resist Pattern Using Radiation-Sensitive Resin Composition for EUV Exposure An underlayer antireflective film having an average thickness of 105 nm was formed by applying the composition for underlayer antireflective film formation on a 12-inch silicon wafer using the spin-coater, and thereafter heating the composition at 205° C. for 60 sec. Each radiation-sensitive resin composition for EUV exposure prepared as described above was applied on the underlayer antireflective film using the spin-coater, and subjected to PB at 130° C. for 60 sec. Thereafter, by cooling at 23° C. for 30 sec, a resist film having an average thickness of 55 nm was formed. Next, the resist film was exposed using an EUV scanner ("NXE3300," available from ASML Co.) with NA of 0.33 under an illumination condition of Conventional s=0.89, and with a mask of imecDEFECT32FFR02. After the exposure, the resist film was subjected to PEB at 120° C. for 60 sec. Thereafter, the resist film was subjected to development with an alkali by using a 2.38% by mass aqueous TMAH solution as an alkaline developer solution. After the development, washing with water was carried out, followed by drying, to form a positive-tone resist pattern (32 nm line-and-space pattern).

Evaluations

The resist patterns formed using the radiation-sensitive resin compositions for EUV exposure were evaluated on the sensitivity, the CDU performance, and the LWR performance in accordance with the following methods. The results are shown in Table 6 below. It is to be noted that line width measurement of the resist patterns was performed using the scanning electron microscope.

Sensitivity

An exposure dose at which a 32 nm line-and-space pattern was formed in the aforementioned resist pattern formation using the radiation-sensitive resin composition for ArF exposure was defined as an optimum exposure dose, and this optimum exposure dose was adopted as Eop (unit: $mJ/cm^2$). The sensitivity was evaluated to be: "favorable" in a case of the Eop being no greater than 35 $mJ/cm^2$; and "unfavorable" in a case of the Eop being greater than 35 $mJ/cm^2$.

CDU Performance

A mask size was adjusted such that a pattern with 35 nm hole diameters and 90 nm pitch was formed by irradiating at the exposure dose of Eop determined as in the evaluation of "Sensitivity" above, and a resist pattern was formed. The resist pattern thus formed was observed from above using the scanning electron microscope. An averaged value of hole diameters at 16 sites measured in a region of 500 nm was determined, the average value of the hole diameters was measured at 500 sites in total at arbitrary locations, and then a 1 Sigma value was determined from distribution of the measurement values and defined as "CDU" (unit: nm). The CDU performance was evaluated to be: "favorable" in a case of CDU being no greater than 2.0 nm; and "unfavorable" in a case of CDU being greater than 2.0 nm.

LWR Performance

A mask size was adjusted such that a 32 nm line-and-space pattern was formed by irradiating at the exposure dose of Eop determined as in the evaluation of "Sensitivity" above, and a resist pattern was formed. The resist pattern thus formed was observed from above using the scanning electron microscope. Line width variance was measured at 50 sites in total, and then a 3 Sigma value was determined from distribution of the measurement values and the 3 Sigma value was defined as LWR (unit: nm). The LWR performance was evaluated to be: "favorable" in a case of LWR being no greater than 2.5 nm; and "unfavorable" in a case of LWR being greater than 2.5 nm.

TABLE 6

| | Radiation-sensitive resin composition | Eop ($mJ/cm^2$) | CDU (nm) | LWR (nm) |
|---|---|---|---|---|
| Example 22 | J-22 | 33.5 | 1.80 | 2.25 |
| Example 23 | J-23 | 34.2 | 1.74 | 2.19 |
| Example 24 | J-24 | 33.1 | 1.82 | 2.31 |
| Example 25 | J-25 | 34.6 | 1.75 | 2.17 |
| Example 26 | J-26 | 35.0 | 1.72 | 2.18 |
| Example 27 | J-27 | 34.5 | 1.80 | 2.35 |
| Example 28 | J-28 | 31.5 | 1.94 | 2.48 |
| Example 29 | J-29 | 32.4 | 1.90 | 2.36 |
| Example 30 | J-30 | 31.9 | 1.92 | 2.42 |
| Example 31 | J-31 | 33.0 | 1.97 | 2.46 |
| Example 32 | J-32 | 35.5 | 1.91 | 2.43 |

TABLE 6-continued

| | Radiation-sensitive resin composition | Eop ($mJ/cm^2$) | CDU (nm) | LWR (nm) |
|---|---|---|---|---|
| Example 33 | J-33 | 33.5 | 1.88 | 2.33 |
| Example 34 | J-34 | 33.2 | 1.84 | 2.26 |
| Example 35 | J-35 | 34.1 | 1.85 | 2.31 |
| Example 36 | J-36 | 32.5 | 1.89 | 2.36 |
| Example 37 | J-37 | 33.7 | 1.81 | 2.26 |
| Example 38 | J-38 | 34.4 | 1.75 | 2.18 |
| Example 39 | J-39 | 34.8 | 1.75 | 2.19 |
| Example 40 | J-40 | 33.4 | 1.80 | 2.25 |
| Example 41 | J-41 | 35.2 | 1.73 | 2.16 |
| Example 42 | J-42 | 33.4 | 1.81 | 2.27 |
| Example 43 | J-43 | 34.5 | 1.77 | 2.20 |
| Example 44 | J-44 | 33.7 | 1.81 | 2.27 |
| Example 45 | J-45 | 34.5 | 1.83 | 2.21 |
| Comparative Example 3 | CJ-3 | 43.2 | 2.89 | 3.56 |
| Comparative Example 4 | CJ-4 | 44.2 | 2.79 | 3.77 |

As is clear from the results shown in Table 6, all the radiation-sensitive resin compositions for EUV exposure of the Examples were favorable in terms of the sensitivity, the CDU performance, and the LWR performance, as compared with the radiation-sensitive resin compositions of the Comparative Examples.

The radiation-sensitive resin composition and the method of forming a resist pattern of the embodiments of the present invention enable a resist pattern to be formed with favorable sensitivity to exposure light and superiority in terms of CDU performance and LWR performance. The compound of the still another embodiment of the present invention can be suitably used as a component of the radiation-sensitive resin composition of the one embodiment of the present invention. Therefore, the radiation-sensitive resin composition, the method of forming a resist pattern, and the compound can be suitably used for working processes of semiconductor devices, and the like, in which microfabrication is expected to be further in progress hereafter.

Obviously, numerous modifications and variations of the present invention are possible in light of the above teachings. It is therefore to be understood that within the scope of the appended claims, the invention may be practiced otherwise than as specifically described herein.

What is claimed is:

1. A compound represented by formula (1):

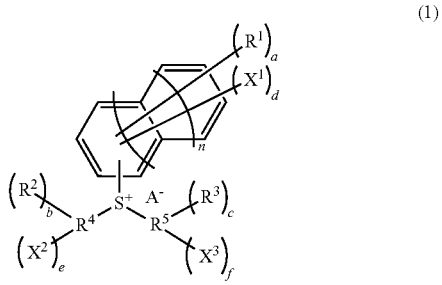

wherein, in the formula (1),
$R^1$, $R^2$, and $R^3$ each independently represent a halogen atom, a hydroxy group, a nitro group, or a monovalent organic group having 1 to 20 carbon atoms;
a is an integer of 0 to 7, wherein in a case in which a is no less than 2, a plurality of $R^1$s are identical or different from each other;

b is an integer of 0 to 4, wherein in a case in which b is no less than 2, a plurality of $R^2$s are identical or different from each other;

c is an integer of 0 to 4, wherein in a case in which c is no less than 2, a plurality of $R^3$s are identical or different from each other;

$X^1$, $X^2$, and $X^3$ each independently represent a group represented by formula (2);

d is an integer of 0 to 7, wherein in a case in which d is no less than 2, a plurality of $X^1$s are identical or different from each other;

e is an integer of 0 to 4, wherein in a case in which e is no less than 2, a plurality of $X^2$s are identical or different from each other;

f is an integer of 0 to 4, wherein in a case in which f is no less than 2, a plurality of $X^3$s are identical or different from each other, wherein a sum of d, e, and f is no less than 1, a sum of a and d is no greater than 7, a sum of b and e is no greater than 4, and a sum of c and f is no greater than 4;

$R^4$ represents a hydrocarbon group having 1 to 20 carbon atoms and having a valency of (b+e+1) and $R^5$ represents a hydrocarbon group having 1 to 20 carbon atoms and having a valency of (c+f+1), or $R^4$ and $R^5$ taken together represent a heterocyclic structure having 4 to 20 ring atoms, together with the sulfur atom to which $R^4$ and $R^5$ bond;

n is 0 or 1; and $A^-$ represents a monovalent sulfonic acid anion,

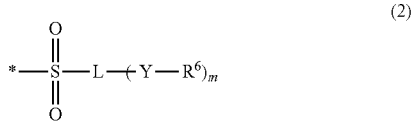

wherein, in the formula (2),

L represents an organic group having 1 to 20 carbon atoms and having a valency of (m+1);

Y represents —COO—, —OCO—, or —N($R^7$)CO—, wherein $R^7$ represents a hydrogen atom or a monovalent hydrocarbon group having 1 to 20 carbon atoms;

$R^6$ represents a monovalent organic group-having 1 to 20 carbon atoms, which is a lactone ring group, a sultone ring group, a carbonate ring group, an alcoholic hydroxyl group-containing alicyclic hydrocarbon group, a phenolic hydroxyl group-containing group, or an amide group;

m is an integer of 1 to 5, wherein in a case in which m is no less than 2, a plurality of Ys are identical or different and a plurality of $R^6$s are identical or different; and

* denotes a site of bonding to a part other than the group represented by the formula (2) in the compound.

2. The compound according to claim 1, wherein n in the formula (1) is 0.

3. The compound according to claim 1, wherein L in the formula (2) represents a hydrocarbon group having 1 to 20 carbon atoms and having a valency of (m+1).

4. A radiation-sensitive resin composition comprising:
a polymer comprising a structural unit comprising an acid-labile group; and
the compound according to claim 1.

5. The radiation-sensitive resin composition according to claim 4, wherein n in the formula (1) is 0.

6. The radiation-sensitive resin composition according to claim 4, wherein L in the formula (2) represents a hydrocarbon group having 1 to 20 carbon atoms and having a valency of (m+1).

7. A method of forming a resist pattern, the method comprising:
applying a radiation-sensitive resin composition directly or indirectly on a substrate to form a resist film;
exposing the resist film; and
developing the resist film exposed,
wherein the radiation-sensitive resin composition comprises:
a polymer comprising a structural unit comprising an acid-labile group; and
the compound according to claim 1.

8. The method according to claim 7, wherein n in the formula (1) is 0.

9. The method according to claim 7, wherein L in the formula (2) represents a hydrocarbon group having 1 to 20 carbon atoms and having a valency of (m+1).

10. A compound represented by formula (1):

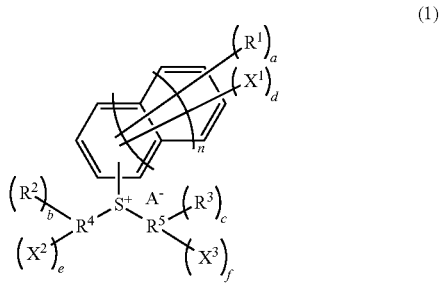

wherein, in the formula (1), $R^1$, $R^2$, and $R^3$ each independently represent a halogen atom, a hydroxy group, a nitro group, or a monovalent organic group having 1 to 20 carbon atoms;

a is an integer of 0 to 7, wherein in a case in which a is no less than 2, a plurality of $R^1$s are identical or different from each other;

b is an integer of 0 to 4, wherein in a case in which b is no less than 2, a plurality of $R^2$s are identical or different from each other;

c is an integer of 0 to 4, wherein in a case in which c is no less than 2, a plurality of $R^3$s are identical or different from each other;

$X^1$, $X^2$, and $X^3$ each independently represent a group represented by formula (2);

d is an integer of 0 to 7, wherein in a case in which d is no less than 2, a plurality of $X^1$s are identical or different from each other;

e is an integer of 0 to 4, wherein in a case in which e is no less than 2, a plurality of $X^2$s are identical or different from each other;

f is an integer of 0 to 4, wherein in a case in which f is no less than 2, a plurality of $X^3$s are identical or different from each other, wherein a sum of d, e, and f is no less than 1, a sum of a and d is no greater than 7, a sum of b and e is no greater than 4, and a sum of c and f is no greater than 4;

$R^4$ represents a hydrocarbon group having 1 to 20 carbon atoms and having a valency of (b+e+1) and $R^5$ represents a hydrocarbon group having 1 to 20 carbon atoms and having a valency of (c+f+1), or $R^4$ and $R^5$ taken together represent a heterocyclic structure having 4 to 20 ring atoms, together with the sulfur atom to which $R^4$ and $R^5$ bond;

n is 0 or 1; and $A^-$ represents a monovalent sulfonic acid anion,

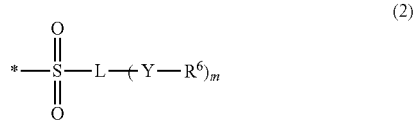
(2)

wherein, in the formula (2),

L represents an organic group having 1 to 20 carbon atoms and having a valency of (m+1);

Y represents —COO—, —OCO—, or —N($R^7$)CO—, wherein $R^7$ represents a hydrogen atom or a monovalent hydrocarbon group having 1 to 20 carbon atoms;

$R^6$ represents a halogen atom-containing group having 1 to 20 carbon atoms;

m is an integer of 1 to 5, wherein in a case in which m is no less than 2, a plurality of Ys are identical or different and a plurality of $R^6$s are identical or different; and

* denotes a site of bonding to a part other than the group represented by the formula (2) in the compound.

11. The compound according to claim 10, wherein n in the formula (1) is 0.

12. The compound according to claim 10, wherein L in the formula (2) represents a hydrocarbon group having 1 to 20 carbon atoms and having a valency of (m+1).

13. The compound according to claim 10, wherein the group represented by $R^6$ in the formula (2) is an acid-labile group.

14. A radiation-sensitive resin composition comprising:
a polymer comprising a structural unit comprising an acid-labile group; and
the compound according to claim 10.

15. The radiation-sensitive resin composition according to claim 14, wherein L in the formula (2) represents a hydrocarbon group having 1 to 20 carbon atoms and having a valency of (m+1).

16. The radiation-sensitive resin composition according to claim 14, wherein the group represented by $R^6$ in the formula (2) is an acid-labile group.

17. A method of forming a resist pattern, the method comprising:
applying a radiation-sensitive resin composition directly or indirectly on a substrate to form a resist film;
exposing the resist film; and
developing the resist film exposed,
wherein the radiation-sensitive resin composition comprises:
a polymer comprising a structural unit comprising an acid-labile group; and
the compound according to claim 10.

18. The method according to claim 17, wherein L in the formula (2) represents a hydrocarbon group having 1 to 20 carbon atoms and having a valency of (m+1).

19. The method according to claim 17, wherein the group represented by $R^6$ in the formula (2) is an acid-labile group.

* * * * *